(12) United States Patent
Chen et al.

(10) Patent No.: US 7,108,978 B2
(45) Date of Patent: *Sep. 19, 2006

(54) METHOD FOR DETECTING A PROPENSITY OF AN INDIVIDUAL TO RESPOND EFFECTIVELY TO TREATMENT OF INTERFERON-α AND RIBAVIRIN COMBINED THERAPY

(75) Inventors: Jui-Lin Chen, Taipei (TW); Yuchi Hwang, Taipei (TW); Min-Pey Ding, Taipei (TW); Wen-Pi Chu, Taoyuan (TW); Shu-Ching Wang, Taipei (TW); Kuei-Ling Belinda Chen, Taipei (TW); Wan-Lin Yao, Taichung (TW); Kuang-Den Chen, Taipei (TW); Ding-Shinn Chen, Taipei (TW); Pei-Jer Chen, Taipei (TW); Ming-Yang Lai, Taipei (TW)

(73) Assignee: Vita Genomics, Inc., Taipei (TW)

( * ) Notice: Subject to any disclaimer, the term of this patent is extended or adjusted under 35 U.S.C. 154(b) by 342 days.

This patent is subject to a terminal disclaimer.

(21) Appl. No.: 10/618,620

(22) Filed: Jul. 15, 2003

(65) Prior Publication Data

US 2005/0014159 A1     Jan. 20, 2005

(51) Int. Cl.
*C12Q 1/68*     (2006.01)
*C07H 21/02*    (2006.01)
*C07H 21/04*    (2006.01)

(52) U.S. Cl. .................. 435/6; 536/23.1; 536/23.5; 536/24.31

(58) Field of Classification Search .............. None
See application file for complete search history.

(56) References Cited

OTHER PUBLICATIONS

Kerr et al. Arthritis and Rheumatism, Sep. 1999. 42(9 Supplement) S336, Abstract 1591.*
Hennig et al. Genes and Immunity. 2002. 3: 359-367.*

* cited by examiner

*Primary Examiner*—Carla J. Myers
(74) *Attorney, Agent, or Firm*—Rosenberg, Klein & Lee

(57) ABSTRACT

It is provided isolated polynucleotides that include sequences from genomic region around the gene CD 81. The polynucleotides include polymorphisms associated with treatment response of HCV patients to interferon-α and ribavirin combined therapy and are useful as the probes in screening for patients who will response to interferon-α and ribavirin combined therapy. It is further provided linkage disequilibrium structure of the CD81 gene and haplotype information within a particular LD block, which can be used for prediction of the treatment outcome of the interferon-α and ribavirin combined therapy on HCV patients.

3 Claims, 17 Drawing Sheets

Table 1: Primers for SNP genotyping of CD81 SNPs with FP-TDI method

| gene/rs | allele | PCR primer name | SEQ ID NO. | PCR Primer 1, 2 | SNP primer name | SEQ ID NO. | SNP Primer 3, 4 |
|---|---|---|---|---|---|---|---|
| rs800146 | R | O1657 | 1 | GAGCGGATTGTGTAACTCTG | | | |
| | A/G | O1658 | 2 | AGGAAGATCTACCCTCACTTG | O1690 | 31 | TGACTGTGGACATCGGAACTC |
| rs2521240 | R | O1661 | 3 | CAGTGTTTCTACTGGCTTGTG | O1693 | 32 | TGGCTTGTGTGTTGAGGGG |
| | A/G | O1662 | 4 | CATTCCAGTGTAGCACTCCT | | | |
| rs800158 | R | O1665 | 5 | TGTGTAACTGTGTATTGGAAAAA | | | |
| | A/G | O1666 | 6 | CTGAGTGTGTCTGTTCCACTTA | O1698 | 33 | AGCCAGTGTCCAATCGTCC |
| rs800163 | Y | O1669 | 7 | GATGAAGGGATATCCAGAGAG | O1701 | 34 | TGGGCTGAATAAGGAAGATCTGTC |
| | C/T | O1670 | 8 | ACCAGGAGTTCTGATGTCTAAG | | | |
| rs800136 | Y | O1244 | 9 | CTGATCATAGGGGAAGAACTATC | O1276 | 35 | TCCCTTCTATTTCTAGTGAGTTCAGTG |
| | C/T | O1245 | 10 | AAAAAGCAACCAAGGTAATAAAT | | | |
| rs800137 | Y | O1246 | 11 | AGAAAGGTCTCTCTGTCAAACAT | O1278 | 36 | CCAAAATGCTGGGAGATGGCA |
| | C/T | O1247 | 12 | TCTTCTCTCCCTGTGTGTA | | | |
| rs1164688 | S | O1252 | 13 | ATTGTGTATTCGTGTATTCAGTG | | | |
| | C/G | O1253 | 14 | AGTTTATGTTGCCAAGGTTAAG | O1285 | 37 | GTACAGTAAATCAGGACAACTTGAAGAG |
| rs2651842 | R | O1256 | 15 | GAGGTTGACAATGGATATCTG | | | |
| | A/G | O1257 | 16 | AGACAGCAAGAGTGTGAGTGT | O1288 | 38 | TGTGTGAAGGTGGGAGTGTG |
| rs800334 | K | O1264 | 17 | CTAAACCAAAGTGTGAAAATTGA | | | |
| | G/T | O1265 | 18 | AGAGCCCTGTCTCAAAATAAAT | O1296 | 39 | ACCTTCTCCACACACCCGA |
| rs2522012 | K | O1268 | 19 | TGGCTAGAGTTGATTGTGTG | O1299 | 40 | CGCTGGGCCGGCTTCT |
| | G/T | O1269 | 20 | GAGAGGGTAGAGATTTGATGTTAC | | | |
| rs2522013 | M | O1270 | 21 | TGGCTAGAGTTGATTGTGTG | | | |
| | A/C | O1271 | 22 | GAGAGGGTAGAGATTTGATGTTAC | O1301 | 41 | CTGGGGAAGGGGCGC |
| rs800335 | Y | O1272 | 23 | TGGCTAGAGTTGATTGTGTG | | | |
| | C/T | O1273 | 24 | GAGAGGGTAGGATTTGATGTTAC | O1303 | 42 | GGGACTTGGGAGGAAGGAC |
| rs800343 | R | O1679 | 25 | CTGGTTGTTGGATGTGTTAAA | | | |
| | A/G | O1680 | 26 | GAAGAATGTTCTTGACTTGAGTG | O1712 | 43 | GGGTTTAATCACAGGCATTAGTGCTG |
| rs800344 | R | O1681 | 27 | CTGGTTGTTGGATGTGTTAAA | | | |
| | A/G | O1682 | 28 | GAAGAATGTTCTTGACTTGAGTG | O1714 | 44 | TGGAAAGGTGGCGGAATTACT |
| rs753136 | Y | O1685 | 29 | CAAAGTGACGTGGAAGAAAC | O1717 | 45 | CCCAGCCCTACAGGTGCAC |
| | C/T | O1686 | 30 | TTCACTCCCTCACAGAAGAC | | | |

Fig. 1

Table 2: Distribution of CD81 SNPs in Chinese HCV infected patients

| SNP | Location in CD81 genome | rs # | Nucleotide substitution | Allelic frequency | Genotype frequency |
|---|---|---|---|---|---|
| 1 | 1949368 | rs800146 | G/A | G=64.3%, A=35.7% | GG=40.7%, GA=47.3%, AA=12.0% |
| 2 | 1953512 | rs2521240 | G/A | G=74.0%, A=26.0% | GG=55.4%, GA=37.0%, AA=7.6% |
| 3 | 1958563 | rs800158 | G/A | G=38.0%, A=62.0% | GG=15.2%, GA=45.7%, AA=39.1% |
| 4 | 1963385 | rs800163 | C/T | C=39.1%, T=60.9% | CC=16.3%, CT=45.7%, TT=38.0% |
| 5 | 1975622 | rs800136 | C/T | C=54.3%, T=45.7% | CC=29.3%, CT=50.0%, TT=20.7% |
| 6 | 1976158 | rs800137 | C/T | C=54.3%, T=45.7% | CC=29.3%, CT=50.0%, TT=20.7% |
| 7 | 1978278 | rs1164688 | G/C | G=65.8%, C=34.2% | GG=43.5%, GC=44.5%, CC=12.0% |
| 8 | 1982077 | rs2651842 | G/A | G=47.8%, A=52.2% | GG=22.8%, GA=50%, AA=27.2% |
| 9 | 1989526 | rs800334 | G/T | G=47.7%, T=52.3% | GG=23.3%, GT=48.8%, TT=27.9% |
| 10 | 1989603 | | G/A | G=54.1%, A=45.9% | GG=29.1%, GA=50.0%, AA=20.9% |
| 11 | 1991149 | | G/A | G=98.9%, A=1.1% | GG=98.9%, GA=0.0%, AA=1.1% |
| 12 | 1991241 | | C/T | C=0.5%, T=99.5% | CC=0%, CT=1.1%, TT=98.9% |
| 13 | 1991254 | rs2522012 | G/T | G=54.9%, A=45.1% | GG=30.4%, CA=48.9%, AA=20.7% |
| 14 | 1991255 | rs2522013 | C/A | C=54.9%, A=45.1% | CC=30.4%, CA=48.9%, AA=20.7% |
| 15 | 1991294 | rs80035 | C/T | C=54.9%, T=45.1% | CC=30.4%, CT=48.9%, TT=20.7% |
| 16 | 191310 | | I/N | I=2.2%, N=97.8% | II=1.1%, IN=2.2%, NN=96.7% |
| 17 | 2009970 | rs800343 | G/A | G=60.4%, A=39.6% | GG=60.4%, GA=0.0%, AA=39.6% |
| 18 | 2010006 | rs800344 | G/A | G=58.8%, A=41.2% | GG=36.3%, GA=45.0%, AA=18.7% |
| 19 | 2020475 | rs753136 | C/T | C=67.9%, T=32.1% | CC=44.6%, CT=46.7%, TT=8.7% |

Fig. 8

Table 3: Association of CD81 SNPs with treatment response of HCV patients to interferon-α and ribavirin combined therapy

| SNP | Location in CD81 genome | rs # | Position in SEQ ID NO. 46 | Nucleotide substitution | Genotype P-value | Allelic P-value | Genotype Odds ratio | Allelic Odds ratio |
|---|---|---|---|---|---|---|---|---|
| 1 | 1949368 | rs800146 | | G/A | 0.3852 | | | 1.32(0.72-2.45) |
| 2 | 1953512 | rs2521240 | | G/A | 0.9473 | | | 1.14(0.59-2.22) |
| 3 | 1958563 | rs800158 | | G/A | 0.6607 | | | 0.76(0.42-1.40) |
| 4 | 1963385 | rs800163 | | C/T | 0.521 | | | 1.29(0.71-2.36) |
| 5 | 1975622 | rs800136 | 1659 | C/T | 0.1079 | 0.0435 | 0.52(0.21-1.31) | 0.54(0.30-0.98) |
| 6 | 1976158 | rs800137 | 2195 | C/T | 0.1079 | 0.0435 | 0.52(0.21-1.31) | 0.54(0.30-0.98) |
| 7 | 1978278 | rs1164688 | | G/C | 0.3676 | | | 1.23(0.66-1.27) |
| 8 | 1982077 | rs2651842 | | G/A | 0.1290 | | | 0.55(0.31-1.00) |
| 9 | 1989526 | rs800334 | 15563 | G/T | 0.0454 | 0.0119 | 3.29(1.07-10.12) | 2.2(1.19-4.07) |
| 10 | 1989603 | pos1989603 | 15640 | G/A | 0.0341 | 0.0101 | 3.61(1.08-12.09) | 2.25(1.21-4.18) |
| 11 | 1991149 | pos1991149 | | G/A | 1.0 | | | |
| 12 | 1991241 | pos1991241 | | C/T | 0.4615 | | | |
| 13 | 1991254 | rs2522012 | 17291 | G/T | 0.0331 | 0.0131 | 0.24(0.07-0.79) | 0.47(0.26-0.86) |
| 14 | 1991255 | rs2522013 | 17292 | C/A | 0.0331 | 0.0131 | 4.19(1.27-13.86) | 2.12(1.17-3.85) |
| 15 | 1991294 | rs800335 | 17331 | C/T | 0.0331 | 0.0131 | 0.24(0.07-0.79) | 0.47(0.26-0.86) |
| 16 | 191310 | pos191310 | | I/N | 0.2103 | | | 0.85(0.12-6.20) |
| 17 | 2009970 | rs800343 | | G/A | 0.8013 | | | 0.87(0.48-1.56) |
| 18 | 2010006 | rs800344 | | G/A | 0.9983 | | | 1.00(0.55-1.81) |
| 19 | 2020475 | rs753136 | | C/T | 0.2933 | | | 1.62() |

Fig. 9

Table 4: CD81-SNPrs800136 alleles and associated treatment response status

| | responder | Non-responder |
|---|---|---|
| CD81-SNPrs800136 C allele | 46 | 56 |
| CD81-SNPrs800136 T allele | 52 | 32 |

$\chi^2 = 4.0764$, P value = 0.0435, OR = 0.54, 95% CI = (0.30, 0.98)

Fig. 10

Table 5: CD81-SNPrs800137 alleles and associated treatment response status

| | responder | Non-responder |
|---|---|---|
| CD81-SNPrs800137 C allele | 46 | 56 |
| CD81-SNPrs800137 T allele | 52 | 32 |

$\chi^2 = 4.0764$, P value = 0.0435, OR = 0.54, 95% CI = (0.30, 0.98)

Fig. 11

Table 6: CD81-SNPrs800334 alleles and associated treatment response status

| | responder | Non-responder |
|---|---|---|
| CD81-SNPrs800334 G allele | 52 | 29 |
| CD81-SNPrs800334 T allele | 40 | 49 |

$\chi^2 = 6.3310$, P value = 0.0119, OR = 2.2, 95% CI = (1.19, 4.07)

Table 7: CD81-SNPrs800334 genotypes and associated treatment response status

| | responder | Non-responder |
|---|---|---|
| CD81-SNPrs800334 GG genotype | 15 | 31 |
| CD81-SNPrs800334 GT+TT genotype | 5 | 34 |

$\chi^2 = 3.29$, P value = 0.0321, OR = 3.29, 95% CI = (1.07, 10.12)

Fig. 12

Table 8: CD81-SNPpos1989603 alleles and associated treatment response status

| | responder | Non-responder |
|---|---|---|
| CD81-SNP pos1989603 A allele | 52 | 27 |
| CD81-SNP pos1989603 G allele | 42 | 49 |

$\chi^2 = 6.6182$, P value = 0.0101, OR = 2.25, 95% CI = (1.21, 4.18)

Table 9: CD81-SNPpos1989603 genotypes and associated treatment response status

| | responder | Non-responder |
|---|---|---|
| CD81-SNP pos1989603 AA genotype | 14 | 31 |
| CD81-SNP pos1989603 AG+GG genotype | 4 | 34 |

$\chi^2 = 5.1402$, P value = 0.0234, OR = 3.61, 95% CI = (1.08, 12.09)

Fig. 13

Table 10: CD81-SNPrs2522012 alleles and associated treatment response status

| | responder | Non-responder |
|---|---|---|
| CD81-SNPrs2522012 G allele | 45 | 54 |
| CD81-SNPrs2522012 T allele | 53 | 30 |

$\chi^2 = 6.1512$, P value = 0.0131, OR = 0.47, 95% CI = (0.26, 0.86)

Table 11: CD81-SNPrs2522012 genotypes and associated treatment response status

| | Responder | Non-responder |
|---|---|---|
| CD81-SNPrs800334 GG+GT genotype | 34 | 38 |
| CD81-SNPrs800334 TT genotype | 15 | 4 |

$\chi^2 = 6.0882$, P value = 0.0136, OR = 0.24, 95% CI = (0.07, 0.79)

Fig. 14

Table 12: CD81-SNPrs2522013 alleles and associated treatment response status

| | responder | Non-responder |
|---|---|---|
| CD81-SNPrs2522012 A allele | 53 | 30 |
| CD81-SNPrs2522012 C allele | 45 | 54 |

$\chi^2 = 6.1512$, P value = 0.0131, OR = 2.12, 95% CI = (1.17, 3.85)

Table 13: CD81-SNPrs2522013 genotypes and associated treatment response status

| | Responder | Non-responder |
|---|---|---|
| CD81-SNPrs800334 AA genotype | 15 | 4 |
| CD81-SNPrs800334 AC+CC genotype | 34 | 38 |

$\chi^2 = 6.0882$, P value = 0.0136, OR = 0.24, 95% CI = (0.07, 0.79)

Fig. 15

Table 14: CD81-SNPrs800335 alleles and associated treatment response status

|  | responder | Non-responder |
|---|---|---|
| CD81-SNPrs2522012 C allele | 45 | 53 |
| CD81-SNPrs2522012 T allele | 53 | 30 |

$\chi^2 = 6.1512$, P value = 0.0131, OR = 0.47, 95% CI = (0.26, 0.86)

Table 15: CD81-SNPrs800335 genotypes and associated treatment response status

|  | Responder | Non-responder |
|---|---|---|
| CD81-SNPrs800334 CC+CT genotype | 34 | 38 |
| CD81-SNPrs800334 TT genotype | 15 | 4 |

$\chi^2 = 6.0882$, P value = 0.0136, OR = 0.24, 95% CI = (0.07, 0.79)

Fig. 16

Table 16: CD81-SNPrs800136 and rs800137 haplotype and associated treatment response status

| | Responder | Non-responder |
|---|---|---|
| CC haplotype | 46 | 52 |

$\chi^2 = 4.0746$, P value = 0.0435, OR = 1.8370

Fig. 18

Table 17: CD81-SNPrs800334, pos1989603, rs2522012, rs2522013, rs800335 haplotypes and associated treatment response status

| | Responder | Non-responder |
|---|---|---|
| TGGCC haplotype | 51 | 43 |
| GATAT haplotype | 30 | 52 |

$\chi^2 = 5.1343$, P value = 0.0235, OR = 1.9767 for TGGCC haplotype
$\chi^2 = 5.4980$, P value = 0.0190, OR = 0.4915 for GATAT haplotype

Fig. 19

SEQUENCE LISTING

```
<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 1
gagcggattg tgtaactctg                                                    20

<210> SEQ ID NO 2
<211> LENGTH: 21
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 2
aggaagatct accctcactt g                                                  21

<210> SEQ ID NO 3
<211> LENGTH: 21
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 3
cagtgtttct actggcttgt g                                                  21

<210> SEQ ID NO 4
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 4
```

```
cattccagtg tagcactcct                                              20
```

<210> SEQ ID NO 5
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 5

```
tgtgtaactg tgtattggaa aaa                                          23
```

<210> SEQ ID NO 6
<211> LENGTH: 22
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 6

```
ctgagtgtgt ctgttccact ta                                           22
```

<210> SEQ ID NO 7
<211> LENGTH: 21
<212> TYPE: DNA
<213> ORGANISM: Artificial Sequence Artificial Sequence
<220> FEATURE:
<223> OTHER INFORMATION: Primer for determination of CD 81 SNP
      genotyping

<400> SEQUENCE: 7

```
gatgaaggga tatccagaga g                                            21
```

<210> SEQ ID NO 8
<211> LENGTH: 22
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 8

```
accaggagtt ctgatgtcta ag                                           22
```

<210> SEQ ID NO 9
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 9

```
ctgatcatag gggaagaact atc                                          23
```

<210> SEQ ID NO 10
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 10

```
aaaaagcaac caaggtaata aat                                          23
```

<210> SEQ ID NO 11
<211> LENGTH: 23
<212> TYPE: DNA
<213> ORGANISM: Artificial Sequence
<220> FEATURE:
<223> OTHER INFORMATION: Primer for determination of CD 81 SNP genotyping

<400> SEQUENCE: 11
agaaaggtct ctctgtcaaa cat                                    23

<210> SEQ ID NO 12
<211> LENGTH: 20
<212> TYPE: DNA
<213> ORGANISM: Artificial Sequence
<220> FEATURE:
<223> OTHER INFORMATION: Primer for determination of CD 81 SNP genotyping

<400> SEQUENCE: 12
tcttctcctc cctgtgtgta                                        20

<210> SEQ ID NO 13
<211> LENGTH: 23
<212> TYPE: DNA
<213> ORGANISM: Artificial Sequence
<220> FEATURE:
<223> OTHER INFORMATION: Primer for determination of CD 81 SNP genotyping

<400> SEQUENCE: 13
attgtgtatt cgtgtattca gtg                                    23

<210> SEQ ID NO 14
<211> LENGTH: 22
<212> TYPE: DNA
<213> ORGANISM: Artificial Sequence
<220> FEATURE:
<223> OTHER INFORMATION: Primer for determination of CD 81 SNP genotyping

<400> SEQUENCE: 14
agtttatgtt gccaaggtta ag                                     22

<210> SEQ ID NO 15
<211> LENGTH: 21
<212> TYPE: DNA
<213> ORGANISM: Artificial Sequence
<220> FEATURE:
<223> OTHER INFORMATION: Primer for determination of CD 81 SNP genotyping

<400> SEQUENCE: 15
gaggttgaca atggatatct g                                      21

<210> SEQ ID NO 16
<211> LENGTH: 21
<212> TYPE: DNA
<213> ORGANISM: Artificial Sequence
<220> FEATURE:
<223> OTHER INFORMATION: Primer for determination of CD 81 SNP genotyping

<400> SEQUENCE: 16
agacagcaag agtgtgagtg t                                      21

```
<210> SEQ ID NO 17
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 17
ctaaaccaaa gtgtgaaaat tga                                              23

<210> SEQ ID NO 18
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 18
agaccctgtc tcaaaaataa aat                                              23

<210> SEQ ID NO 19
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 19
tggctagagt tgattgtgtg                                                  20

<210> SEQ ID NO 20
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 20
gagagggtag gatttgatgt tac                                              23

<210> SEQ ID NO 21
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 21
tggctagagt tgattgtgtg                                                  20

<210> SEQ ID NO 22
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 22
gagagggtag gatttgatgt tac                                              23
```

```
<210> SEQ ID NO 23
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 23
tggctagagt tgattgtgtg                                             20

<210> SEQ ID NO 24
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 24
gagagggtag gatttgatgt tac                                         23

<210> SEQ ID NO 25
<211> LENGTH: 21
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 25
ctggttgttg gatgtgttaa a                                           21

<210> SEQ ID NO 26
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 26
gaagaatgtt cttgacttga gtg                                         23

<210> SEQ ID NO 27
<211> LENGTH: 21
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 27
ctggttgttg gatgtgttaa a                                           21

<210> SEQ ID NO 28
<211> LENGTH: 23
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 28
gaagaatgtt cttgacttga gtg                                         23

<210> SEQ ID NO 29
```

```
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 29
caaagtgacg tggaagaaac                                              20

<210> SEQ ID NO 30
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 30
ttcactccct cacagaagac                                              20

<210> SEQ ID NO 31
<211> LENGTH: 21
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 31
tgactgtgga catcggaact c                                            21

<210> SEQ ID NO 32
<211> LENGTH: 18
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 32
tggcttgtgg ttgagggg                                                18

<210> SEQ ID NO 33
<211> LENGTH: 19
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 33
agccagtgtc caatcgtcc                                               19

<210> SEQ ID NO 34
<211> LENGTH: 24
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 34
tgggctgaat aaggaagatc tgtc                                         24

<210> SEQ ID NO 35
<211> LENGTH: 27
```

```
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 35
tcccttctat ttctagtgag ttcagtg                                          27

<210> SEQ ID NO 36
<211> LENGTH: 21
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 36
ccaaaatgct gggagatggc a                                                21

<210> SEQ ID NO 37
<211> LENGTH: 28
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 37
gtacagtaaa tcaggacaac ttgaagag                                         28

<210> SEQ ID NO 38
<211> LENGTH: 20
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 38
tgtgtgaagg tgggagtgtg                                                  20

<210> SEQ ID NO 39
<211> LENGTH: 19
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 39
accttctcca cacacccga                                                   19

<210> SEQ ID NO 40
<211> LENGTH: 16
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 40
cgctgggccg gcttct                                                      16

<210> SEQ ID NO 41
<211> LENGTH: 16
<212> TYPE: DNA
```

```
<213> ORGANISM: Artificial Sequence
<220> FEATURE:
<223> OTHER INFORMATION: Primer for determination of CD 81 SNP
      genotyping

<400> SEQUENCE: 41
ctgggggaag gggcgc                                                    16

<210> SEQ ID NO 42
<211> LENGTH: 19
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 42
gggacttggg aggaaggac                                                 19

<210> SEQ ID NO 43
<211> LENGTH: 26
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 43
gggtttaatc acaggcatta gtgctg                                         26

<210> SEQ ID NO 44
<211> LENGTH: 21
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 44
tggaaaggtg gcggaattac t                                              21

<210> SEQ ID NO 45
<211> LENGTH: 19
<212> TYPE: DNA
<213> ORGANISM: Artificial Sequence
<220> FEATURE:
<223> OTHER INFORMATION: Primer for determination of CD 81 SNP
      genotyping

<400> SEQUENCE: 45
cccagcccta caggtgcac                                                 19

<210> SEQ ID NO 46
<211> LENGTH: 26017
<212> TYPE: DNA
<213> ORGANISM: Intelligent human being
<220> FEATURE:
<221> NAME/KEY: allele
<222> LOCATION: 1659
<223> OTHER INFORMATION: CD81 SNP genotype, for detecting propensity of
      individual to response effectively to treatment of interferon-?
      and ribavirin combined therapy
<220> FEATURE:
<221> NAME/KEY: allele
<222> LOCATION: 2195
<223> OTHER INFORMATION: CD81 SNP genotype, for detecting propensity of
      individual to response effectively to treatment of interferon-?
      and ribavirin combined therapy
<220> FEATURE:
```

```
<221> NAME/KEY: allele
<222> LOCATION: 15563
<223> OTHER INFORMATION: CD81 SNP genotype, for detecting propensity of
      individual to response effectively to treatment of interferon-?
      and ribavirin combined therapy
<220> FEATURE:
<221> NAME/KEY: allele
<222> LOCATION: 15640
<223> OTHER INFORMATION: CD81 SNP genotype, for detecting propensity of
      individual to response effectively to treatment of interferon-?
      and ribavirin combined therapy
<220> FEATURE:
<221> NAME/KEY: allele
<222> LOCATION: 17291
<223> OTHER INFORMATION: CD81 SNP genotype, for detecting propensity of
      individual to response effectively to treatment of interferon-?
      and ribavirin combined therapy
<220> FEATURE:
<221> NAME/KEY: allele
<222> LOCATION: 17292
<223> OTHER INFORMATION: CD81 SNP genotype, for detecting propensity of
      individual to response effectively to treatment of interferon-?
      and ribavirin combined therapy
<220> FEATURE:
<221> NAME/KEY: allele
<222> LOCATION: 17331
<223> OTHER INFORMATION: CD81 SNP genotype, for detecting propensity of
      individual to response effectively to treatment of interferon-?
      and ribavirin combined therapy

<400> SEQUENCE: 46
gagacatggt ttcaccatgt tggccaggct ggactcaaac tcctgatctc              50
aggtgatcca ctcgcctcgg cctcccaaac tgctgggatt acaggtgtga             100
gccactgcgc ctggccttcc taaggatatc ataattttag tgcttacatt             150
taggtctacg atccattttg agttaatttt tgtgcacagc atgaggtagg             200
ggtccaactt cattcttttg cacatggata tctagttgtc ccagcaccat             250
tttctgaaaa gactattcct tcccccattg aattgtcttg gtaccttgt              300 caaaaatcaa ctgatggccg gtctgaaggt agtgagttat ctcaattgat             350
tgttcacagt cagttacaga tggaacacct cgttctactc tttcccgcct             400
tctcactgct gcacttgaac agtctttaaa aaaatcaatt gaccataaat             450
gcaaggattt gttcttggag tctcaacttt actgcattga tctgtaggtc             500
tatccttatg ccagtaccac attgtcttga ttactgtagc tttgcagtaa             550
gtttgaatca ggaaatgtga gccctccagt tttgctcttc tctttctaga             600
ttgttttggc tattctgaaa cccttgtatt tccttatgaa tttgaggatc             650
agcttgtaaa aagacagatg ggattttgac agagattgtg aagctataga             700
tgaattcggg agtttggcca tcttaacatt atgtctcctg atccatgact             750
gcaggatatc tttccattta attcgatact ctttgattcc tttcaaaaat             800
attttgtatt tttcagtaca caagttttat gcatcttttg ttgcatttat             850
ttctaggtat gttctttttg ccaatattat aaatgagatt gtcttcttca             900
cttcattttt ggatggttca ttgctagtgt atagaaataa aatcgatgtt             950
tgtatattga tcttgtatcc tgccacattg ctatgcatgt ttattagttt            1000
taagggtttt agtggatttt ctatatataa tgtcatataa tcagcaaata            1050
gaaagtttaa tgtcttagtc cttttgagct gccacaacag actaccataa            1100
actgagtggc ttataaacaa cacaaatgta tttcccacag ttctggagac            1150
tgggatgtcc aagatcaaga cacccgtagg tttggtgtct ggtcggggcc            1200
```

|  |  |
|---|---|
| tacttctggg ttcatagatg actgtcttct cgctgtgtcc ccccccatagt | 1250 |
| gaaaggaagg ggcccagggt cttcctaagg cttcttttat aaggacacta | 1300 |
| atccaatata ggaaggctct gccctcataa cctaatctcc caaaggcctc | 1350 |
| acttccaaat tccatcacct ggggagtaag aatttcaaca ctgggggac | 1400 |
| acagatattc agacatagca ttttcttct tcctttctaa tatgggtgcc | 1450 |
| cttgacatct ttttcttacc taattgccct gccagagcct tccagacagt | 1500 |
| gttgaatgga agtggggagc attcacccca ccttactcct gatcataggg | 1550 |
| gaagaactat ccggctttca ccactgagca ccacgttagc tgggtatt | 1600 |
| ttgtcagcgc tctttatcag gtggaggcag gtcccttcta tttctagtga | 1650 |
| gttcagtgyt ttttttttt tttaatcagg gaagagtgtg agcttgtgtt | 1700 |
| tgggtgcctt ccctgcgtct gttgagatga tcttacggtt tctgtctctt | 1750 |
| attctattga tatggcgtat ttattacctt ggttgctttt tggatgttga | 1800 |
| taacatccaa actcttctgc cacccctttt aatagaaagc tgtacaactc | 1850 |
| cccaacctgc ctgggcgtgt ctgcccaaga tgagtgctag tggccgactc | 1900 |
| cctgctagag tgagcactgc ataaacagcc tctgcttgtc ctcatttgag | 1950 |
| tgatcttcat gtattccacg agaaatcaag gcacaggggt ctcatggtct | 2000 |
| catgaatggc tccaccaact gaaggtgtgc tccatcgggg ctgtgagtca | 2050 |
| cctcacgcca ggcagaaagg tctctctgtc aaacatggct tcaaggaacc | 2100 |
| agggacctgg ttcctcccac aggccaggcc ctgcccctaa gtgcaatggg | 2150 |
| aatatatgca catgtcacct gtcccaaaat gctgggagat ggcayttctg | 2200 |
| cagatgggga aactgaggga ccagcccgaa gtcacgggga ggggaagact | 2250 |
| cctacacaca gggaggagaa gaacccagcc gggctgcaaa cgcctgccct | 2300 |
| tcctcaacgt gcctccggct gtgcccacat cgctccagca gctctgcctt | 2350 |
| cctcaggcat aagccttctc agggcagggg aggcccaggg agcggcgctc | 2400 |
| ccatcccagg ccgggctgct gagcaagccc ctccccttc tcccctcatc | 2450 |
| ctctgacaga gtccacctga atatttgtcc tggagccagg atggaagctc | 2500 |
| caccaggccc agctaacaac aggaacccctt tcagacgcac ttctgggtgc | 2550 |
| gtactgtgcc agtatcacac agacacaagc catgtccttg tcagccatgg | 2600 |
| gatccccaag gtccccatga ggtcacacca gtgggccact gggaagggca | 2650 |
| cttcagatgt ggagctccca tgggccaggc ctgcgaagt ggtcctccta | 2700 |
| cccccctcata gccagtcttc cctgtgagcc tgcaagtgac tgtgaatgtg | 2750 |
| agttccactc tggagctaag acgggctgct gcccccgcaa tcagatgtca | 2800 |
| ggcccatgaa gccctccatc atcccactgc agtcagaata aaatgcagcc | 2850 |
| tccctctggc ctccaggtcc caaggccagc ccccctgcct cccaggctca | 2900 |
| cacctgcccc taacctgtgt ccagcccctt tccctggct ctgtctcctg | 2950 |
| cttccttgt gttcctccaa cctcacctgt ctgtctggag tgctcctccc | 3000 |
| cggctctgcc tagctggctc cttctcaggc atcagggcct ggatccactg | 3050 |
| tggctcttcc aagcctctgc acttggagtg cctcagcccc gtggttgagg | 3100 |
| agtgccccaa ccctgtgacc ctctagcaag catcctagga attccgtccc | 3150 |

| | |
|---|---|
| tccccagcac tgatatgacc atcgtgctgt gacacgtgtc atctccgcca | 3200 |
| gagttgcaga tcctccaggg gagggtctg ctgcctggct cccacagcca | 3250 |
| gggcctggaa cagtgcctga cacacagcag gcacccacta aatatttgat | 3300 |
| gcatggctga agaggacagg caggctggct gctggctggg catggcctgc | 3350 |
| ttctgaggct ggtggtcaag gacacagtgt gcatggatct gccccctcct | 3400 |
| cccacttcct gagagtggag ccagtgtctc cctccaccta ccgcccctg | 3450 |
| ctgaggacac agctcacacc tttaacggga aatgtcccca tcactgggga | 3500 |
| cagcagggag ctgatgggag agcaggtgtc caggacatcc agagaaatgt | 3550 |
| ttcctcacac tggaacccTt ttctattccc ttctaaacaa aaagaatcct | 3600 |
| cgaagactct caagtgacca tatagtgtct tttcttataa tgtcacttcg | 3650 |
| acaggcacaa aatgtaaaac caggcataaa ctactagtgc ttgcagttct | 3700 |
| tacgcaggca tgaagccaaa accagtttac aaattaacca ccaagaaaac | 3750 |
| cggtagagca cagatgatga cgatagagct gttttgtcca atgtgagcgc | 3800 |
| tactggccac ccagggccat gtgaatttaa attacgatga aacacaatga | 3850 |
| aaaatttggt tccttgtggc cacatttcca gtacccagta gtcatctgtg | 3900 |
| ccaggggtt atccaggtac agaacattcc catcgttgca gaaggttcta | 3950 |
| tcagctagca ctgggttgga cgacacttgc caagacgagc tggctagagg | 4000 |
| atggttctcc ggacctggtc ccacgtggtt cccaggtaag cccccgccca | 4050 |
| ggatgcagcc ccgttgtcca tcagtttTct tggagagggc atgggaaacc | 4100 |
| ttcgtcagtg tgtcatctcc tgcaaaggcc ttcgctcctt cctctgggga | 4150 |
| gaaagcaccc ttcactctct gaatcattag cccaaagcag taagtgcagc | 4200 |
| aggcctggcc ccacaccttc cggaagagcc acggtgtgag gctggcatcc | 4250 |
| ctggggcacg acacaaccag gatgtagacg aaatagatgc aatatctgga | 4300 |
| ggttctccta taggtgtctc tggcctcctg gacacttcac actgttctgg | 4350 |
| gagctgccct ctcaggcccc agtgacccttt tcagatgcag actcccacag | 4400 |
| catgggtcag caattctccc cttccgtgag acagggattg gttacctgta | 4450 |
| ctaggacctt gaggccaaca ctgactaggg ggcctcatgc ctgcccaggt | 4500 |
| tccagccccg gagagcaatg tgagcaaagc ttgctgtctt tgcaaagcca | 4550 |
| accactgtgg catcaactcc ttcaggaagc cctcccggat tgtccaaggt | 4600 |
| gctcacctcc tttggggagc cctcccagat tgtccaaggt gcttgaggga | 4650 |
| gggaggaatg ggttgttctc ccggcaccgg ggctgcactc ctgggcagac | 4700 |
| gctgcatgcc tgtcctcagg cgcggccctg ctgccacccc cttggggggct | 4750 |
| cggagcgcga cagcagcttg gggacgcctc ccgcgcccag cacggtgcac | 4800 |
| ctgggccctg aggtcctggc cgaaacgcgc caagttgggg gtaggtgcag | 4850 |
| cgaccccata cccctcggct gcgcgccctg gcggcaggag gcggggccgg | 4900 |
| gggcggggcg tgagctggcc ggggcggggc ctatggaggg gcgggaccgc | 4950 |
| ggcgccctat aagtactgcg gagcgaggcg cgcgcccggc cagagagcga | 5000 |
| gcgcgcaacg gcggcgacgg cggcgacccc accgcgcatc ctgccaggcc | 5050 |
| tccggcgccc agggcgcacg gcgcgccccc gtgccggcgg ccctgcgcc | 5100 |
| catttcttgg cgcccccgcc cggtcggccc gccaggcccc tttgccggcc | 5150 |

-continued

| | |
|---|---|
| accagccagg cccccgcgccg gcccgcccgc cgcccaggac cggcccgcgc | 5200 |
| cccgcaggcc gccccgccgcc cgcgccgcca tgggagtgga gggctgcacc | 5250 |
| aagtgcatca agtacctgct cttcgtcttc aatttcgtct tctgggtaag | 5300 |
| ggctgcgccg ggggccgggg cgggaggggg caggcacaca ctccacgttg | 5350 |
| ggcaggtccc gcggcagcgt gctaggcccc gcgggcgcag cgccgggccgc | 5400 |
| gaagttgtgg ggccacctgt gggctccagg agcgggtgg ggggtcgccc | 5450 |
| ggggccaccg cgcccccccga cattgggggct gagggctgcg agccgagttt | 5500 |
| cggggcctct gtgctcgggg gcccacctct gcggccgggc cggggcttct | 5550 |
| gggggccgcc gggcagttcc cgctgtggtg gtgatgggtg cggtggtcgc | 5600 |
| gggtcgggac ccgagtaccc ggccgcccct cagctaagga ggggcctgcg | 5650 |
| cgggtccctg gccgcggatt ccggactgct gcttcgcggg gacgaggggg | 5700 |
| gggctcgcgg gcgggactcc tggcgccccg cccccatgag ctcatcaaga | 5750 |
| gccgccgccc ctggatggtg gggcgggggc gcacactttg ccggaggttg | 5800 |
| ggggcgatcc gcctcactct ttccccagcc cagctcactc tccaatctgc | 5850 |
| ggtcaccacc cgagaccttc ctgggggtcg cgcctaaaag gagcgcagac | 5900 |
| tcccgccggg atggcccaga agctggggtg cgcgcaccct ggccgtccct | 5950 |
| gcctgggagc cgatctccct ctcctcaccc agacacgttc cagcggaggc | 6000 |
| ctcctcccag aagggctctg gaggcctcgc aggagtgggg atcccgcggt | 6050 |
| tctgagttgg cacaaggaag agagtggcac caggggcctg gagtggatgg | 6100 |
| cagggtctgg gagtggggcc gctgcttttgc aagaggggcc cccacgctgg | 6150 |
| gcatctttgg gtgccagcgt gggtggagga gggtcttttg ctgagaatgg | 6200 |
| ctttctcctg accgcagtct ttgctgctgg gaagtgactg atgggctatc | 6250 |
| gccttttgtt tccattctcc tgtcggtgtt agaattgggg aggggggtgga | 6300 |
| aatcccttct tggcctggaa ggactggagt gggtgtccat ggccgcggcc | 6350 |
| tccccgtggc cacgcccctg ggcatagact gcaagcccct ccccgtgccc | 6400 |
| cccaggctgt cacccccttc tcgtggaaga ctcggctgat gtcccagtgg | 6450 |
| accgagtgtt tctcaagttg aggcagggag ggcaaacttt ttaaatggcc | 6500 |
| cctggagcca gtgtgtggga ccagagacat ctgtttccca tctggacggc | 6550 |
| tgaggatccc agtgcggatg attatttgga gggggaagga cggaggctga | 6600 |
| actgaactct tagctgggag atgagtgggg cagtcacatc ccaccttccc | 6650 |
| caagccgggc tgttctgcac agcctgcttg ggacgctggt gggagtcact | 6700 |
| gtggcctttcg gcactgccct ggcagtgggg gcagctaggc catttgggag | 6750 |
| gggctcgcct tccccaggcc cggccctggg acctcagcgg ttgcttagtg | 6800 |
| gtggcctgct tcagcccagg catgtgggag aggcaccaga cacaggatgt | 6850 |
| ccctctgcca gcccctgaag ccccgtcccc tgacgaggcg agtgtggacc | 6900 |
| tgggggtggg ggctgaggga gactgtggac ctggggtgg gggctgaggg | 6950 |
| aagtgtgga cctgggggca ggggccgagg gagggtgtag gcctgggggt | 7000 |
| agtaggggct gagggagagt gtggacctgg gagtaggggc tgaggagggg | 7050 |
| tgtaggcctg ggggtggggg ctgagggaga gtgtggacct gggggtaggg | 7100 |

-continued

```
gctgagggag tgtggacctg ggggtggggg ctgagggagg gtgtggacct         7150
ggggcaggg gctgagggag agtgtggacc tagggcaga ggctgaaggg           7200
gagtcacggg aggggacttc tccggaggtg gattttgct ctctggacgg          7250
tgtgtcagca ctggtgagc ccctcctgcc tgcccaggct gagaggtctc          7300
cctggcagcc ccctgggagt gtcgccaggg cgggcctgga agtttccag          7350
gcagctgggg tggagacctg acacatccca agggtgcttg ttattaaggc         7400
tcaaggaaat gtctctgagg cctcaccgct cctctcccca gggcctgctc         7450
cctgcaaagc attgagaact gagtccgtcc acagtcactg tggacccacc         7500
catccactgg ggctcagtgg tagccagcaa tgccaggctg ggtgaggtgg         7550
ggttggtggg caccaccctg gtgaccccc ctccaccctg gtgccgcagg          7600
gtgtgtggct gagagcacag tgccatgggc ttgggcctcc ttggtggagt         7650
ccccaacaca ctgctctggt cctgggcctc ggccttcccc gtctgcagtg         7700
ggggcccaca gtgagcctac ctcctggtgg tgttggtgga tttgctgaca         7750
tgcctgagtg ttgacagggg gcttggtgca ggaagggctc agggcgtggg         7800
tgttggccag gggtccaaag ggacctctgc ctcagagagc ccagcccaga         7850
caggcaggat gtgcagtggg gaaggggctg cgggaaccct gcagggtcca         7900
gaaggacaca gtgcagtcct gtgggctctg gggaggctgg tggggaggag         7950
gttgacaatg gatatctggg tgggcactt gttagaagtt ccattttaga          8000
gaggaaagag gccttgcctg tgggagaagg cagctggggt agcctgacct         8050
ctttcccagg aaggagccca cacacacacg cacaggcact cacacacacg         8100
aatgtgcaca cacgcacact cccaccttca cacacactca cactcttgct         8150
gtctcccttc ccaagccaag gtgcgagggg gaaggtctgg gcagcatgca         8200
cctgcgccct gaccgctttg ggggccagtg agaactgggc tccctgggtg         8250
cgtggcgggc ccaagcaggg aggacattgc agatgccctg gccaagcagc         8300
gtggaaatcc tgtcccttgg gtgggtctcg gagcctccat cagaggcggc         8350
tggcacctga gacccacctg ctgccaggag cagggcagga gagtttgtgt         8400
cccgggacag ggaactggcc tgtgggagcc ttgccttcct catctgtgta         8450
atgatataa gagtcttctc ctcgggggct ggccagggag tccagaagag          8500
gtgtcaccag tccccgcagg gagaagagcg gtgtcccccg cctgggactg         8550
gctgctcccc caagctaatg cagctggtag ccacctccca gtggcagggc         8600
agccaaaccc ggccgggaaa gagactgatt agaagcctcg ctcacgggta         8650
tttctcgctt ccagacagca catgactgtc atttggcacg tctttcgccg         8700
tccttccggg agaggggctg caaccctggc aggcgctgtg gggagggggg         8750
ctaggacatc ctgtgcctgg tttcaccaag tgggtgtgtg gactttccct         8800
ggctcccca ggctgtctgg ctgcacagct ttggggaaac ggccactggg          8850
tcaagcgggc cgagaagagg aagtctgtgg tttgtctctg ctacagactg         8900
gccccagtga ggctgtccag cagtgcaggg cacagagcaa aagcagggag         8950
gtatgggcct acttccccgg tcgcccctgt ggctggctgt ggctctgccg         9000
ggtgctgaca agtcactcgc cctccctgcg gtcaccaggg tgcatgcccg         9050
aaagccctcc attctttcct gggtttgagg gtccttctcc tgcacccacc         9100
```

-continued

| | |
|---|---|
| ccagcgccca gttcagctca actttcagaa atctggttca cccccaatcc | 9150 |
| ctttctcata actgcttcca agcccagaca aggagacaga ccccagaaga | 9200 |
| tccctacccc tatttccgca cctgaaatcg caccacggga agagctttgc | 9250 |
| tcatagagtc aataaggctt agagtccagg cgcctgtgcg agggagcagg | 9300 |
| tcatcaccct tgtacccacc gtggttttag acaggaccct gaggttgggg | 9350 |
| tggggctggg gctggagagg agccaggtgc cctgccccctt gcttgggccc | 9400 |
| cgtgtccctg tgatccaggc tgggcgtgct atgggtgctg ggtgatattc | 9450 |
| cagccctgca ggtgtccgcc ttgttcccag caccctctg ggcaagaaga | 9500 |
| accaggctct cccagaaatg ggcttcagtg atctccactt ccaagtcgtc | 9550 |
| cccacctgcc ttgtaggaca cagtggtacc tggtatgctg ggcagccttc | 9600 |
| caggaacctc tggacttact cagtgtcccc cagccctaca caccattctt | 9650 |
| tgtgtttctg ggcccaaact aagcccccca acctgggctg cagagcaagt | 9700 |
| gctgaatcat gagagaccct tgagggtcct ccaggtaggc ccccagtgct | 9750 |
| ggaggagtcc cctcaggcag ggggccacgc ccaagggtgt ggaaggtcag | 9800 |
| ctggcagccg gatctcactt ttggggctgt aggcttcctg cactggccgc | 9850 |
| caatgccatg gccgtgggat ggccaggata aggcatctgc cccccacccc | 9900 |
| caccccccgc acaaggtctt tgagggctgc gggctcaagg agttggcggt | 9950 |
| agggctgggg gaccaggggc acagagcttg taagcgcctc tctccaggat | 10000 |
| gtgggtggcc cagcagggga gctttgagag tccaggtgtg agattccaaa | 10050 |
| tgctaggggc ctgagaggag ggagccacca gcttggccag agcctggtgg | 10100 |
| atcacgcccc caccacgcct tgcccttctc tctggtcatg tgctctccca | 10150 |
| ccacgtttgg aaagttactg cttccctctt cctcagcccc tcgggctccc | 10200 |
| agttatggaa gtggcgtgat tcagagaagg taaaggatgg gagggagagg | 10250 |
| gctgggtgat gggggacccc gcagggcgcc ctgtgctgtt acatggagct | 10300 |
| ccaggatcag ggcaggtggg cagcctgggg tcctcacttc tctccccagc | 10350 |
| caggccaggt ccctcacagc cctgccagga gcatgtatc cgctgcggtg | 10400 |
| cagaactaat ctcaaagctc aaacccaggt aacagtgtag gtaaaacaga | 10450 |
| tgacagggca tgagactcac cccaggacag gcgaaggacc caggccgatg | 10500 |
| ggggcccaga acagtcctga tcctggagct ccttcccgag tgggacccca | 10550 |
| ggggtttccg aggggcttag agtagggctt agaggcttag agtagggcta | 10600 |
| gggacttcct ggcttccctg cctcgggaac agctggtcct ggaaggggct | 10650 |
| tggtcctcgg ggcactggtg cccaccaccc ctgatgcctg ggagacacca | 10700 |
| gcatcctctg agcatgtgtg cgtcctcctg gtcccgaggg aagtgactcc | 10750 |
| tcacatcccc cagctggcgg ggccagaggg ccagcatcct cgcctgacac | 10800 |
| ctatttttag atgctgagac aggcggcttc ctcggggcca ggggccctgt | 10850 |
| ttgagtggag cttccgcttc ctggcctagg agagaattcc tgctcctctt | 10900 |
| ccctccatgc tgccttttcg cccctggagg ccacaacggg gtcagagggg | 10950 |
| cagctgctca ccacctagga gggcctgaga gggccctacg tcacccaggg | 11000 |
| aggagtctgg ccccgtcccc aacctccaca cccaggcctg gcactgcccc | 11050 |

-continued

| | |
|---|---|
| ttattggtgg gcagagagtg aggggttggc ctgcagggac ccaggctgga | 11100 |
| ggggccgttc acctccggcc cccagcgtcc cttcctggaa gcaccttggt | 11150 |
| gagcccctcc cctccttcac ccagtatctc caggggtact tcctcctttc | 11200 |
| cttcctgcct cagggcctca ctgtcctcct ggggagggtg tctcaggccc | 11250 |
| cagcacctcc cagtggctga gccgaatggg cacttcccgg tgtgtttccc | 11300 |
| atatgtgcag tccctaggtg tcggtgagca ggcacagagc ccgcagcgtg | 11350 |
| gccctgcctg gtggaccccc tccccaagag catcaaggga gggcctggac | 11400 |
| tagagacaca cagatgccca gcctgtacgt aaaggcgggt gagctgatgt | 11450 |
| accatcgtcc tcgtccccca ctgggtgcc tgggcaggac ttggggtgac | 11500 |
| cacttggccc gtctgggtgg gggtaagata tgggtggggc gaccagatcc | 11550 |
| ctgccctttc ctgcagctgt gggggtgtgt gtgctggcct ggagagctcc | 11600 |
| cacccgaagt tctggctcct ggctgtccgg ggctgcggg ggcagcgagc | 11650 |
| agctggcatg ggtaggggag ctgacctagg cctgcccggg cagcgcctgc | 11700 |
| tgccttttgc tcccttttcag ctgcttcttg gaaacagcgg acaggctggg | 11750 |
| caggaaccca gtgtgcttgg cagcccccct tttaaagtcg attctgttat | 11800 |
| ttattaattc ccaggaagga gaaagaaaga aacaatcctt catagagtac | 11850 |
| aaacactgct tttagtagcc ttgcaaggag ccctccagga accccacagg | 11900 |
| ttacctgggc tccatcctga gagccaccct ccatccccaa tccccagcag | 11950 |
| agcatcttgt ggggtggggc ggcttgtggg gcggggcgcc ttgggaggcg | 12000 |
| gggtgtctcg ggaagcgggg cgtctcggga ggtggggtgg cttgtggggt | 12050 |
| ggggcatttc ctggggtggg gcgtctcgtg gggtgggaca gcttgggggg | 12100 |
| tgggcatct cggagggcgg ggcgtcttgt ggggtagggc ggcttgtggg | 12150 |
| gtgggcatc ttgtggggta gggcggcttg tggggtgggg catcttgtgg | 12200 |
| ggtgggacgg cttgtggggt ggggcatctc gtggggtggg gcatctctgg | 12250 |
| ggcccggcca cttgggaggc ggggcatcct ggggggcgggg catctcagag | 12300 |
| ggcgcctccg gaggctggag tatcttggga ggtgggagca ggtggcagag | 12350 |
| aggcttccca caggtgagct ttgagcaggg aggtgcctgt atggatggct | 12400 |
| ctgtggggag aggggtgaca ggagttccag attccggcac ttatgaaacc | 12450 |
| tcacagtgat ggagagccga gtgctgctgt gcaggctaag ttgtgtgcat | 12500 |
| gtcagcttct gcactttat ttccttgttt gtagacaagg cagagagaag | 12550 |
| ctgagatggg cctgaggtcg ccttggtgaa aggcactcag cagccagggc | 12600 |
| cttgggctgc cctccctcat caccgtgaaa gcgggactct cttttaactg | 12650 |
| acatcgggct ccatagttac tccagtccta actttgatgg atcctaaaag | 12700 |
| tgcacttcta aggacgcggc ttcggtgttt cccatgccgc tgcttgcccc | 12750 |
| tgggaagcgt tggctctgcc tcggaagaag ttagcgccaa gatggcagcc | 12800 |
| tggggtcttt ggggcccaga agaaacactg gccccgggga gttcagtcat | 12850 |
| cagggactta ggatgtgggg cttttcaaa cagctttatt tagacgtgat | 12900 |
| tgacacacag taaatacaga tgtttaaggg tacaacttgg taagttttga | 12950 |
| caaatttata cccccgtgaa accatcacca actccccagg tgcccctggg | 13000 |
| gcccttggga tctctgcttc ctgcccctcc tccccgtccc aggcaacca | 13050 |

-continued

| | |
|---|---|
| cgggccgtcg ctgtgggtgc acacagcatg catttcttca acaagcggac | 13100 |
| tcagaaggca cttgcacatc gttgctgttc tgcctctttg cttcagcatg | 13150 |
| attacccaga ggcgcacccg tgccgtggcc tgcccgtcgt ctatgcaccc | 13200 |
| gtgctgtggc gtgcccgtcg tctgtgtggc atgcctgtct gtgcacccgt | 13250 |
| gctgtggcgt gcccgtcgtc tgtgtggcat gcctgtctgt gcacccgtgc | 13300 |
| cgtggcgtgc ccgtcgtctg tgcacccgtg ctgtggtgtg cccttcgtct | 13350 |
| gttcctttta ttgccgggca gggttgcacc cacatgtgca agccagcgac | 13400 |
| ggaccccagg ttcacccgtt caccggtcag tgggcatatg ggttgtttca | 13450 |
| gtttggggca tttacaagaa acgttgctag aacatttgtg tacaagtctt | 13500 |
| gtgtgaacct aagttcattt ctcttgggta atacctgtg cgtggagcag | 13550 |
| ctgggtcatg tggtgaatgt gggtttcact gcttaagcag cagttttaca | 13600 |
| taactgccaa actgttattc aaggtggctg gaccgtttta cagcccccgt | 13650 |
| tgtatgcgtc ccagttgcct cccccagcag catgtggtgt ggttggtctt | 13700 |
| tttcgtggca gccagtccac tgggtgcgct cggcatgtgg ctgcagcttg | 13750 |
| acctgggttt cctggtccct ggcaaggtgg agcatctctt catgtgcttt | 13800 |
| tttgctgtgt gtggatcttg cggggaaggg tctgttcctg ttttttgccc | 13850 |
| atctttcaaa gattggggttg ccagttttct tgctgttgag tttggaaagc | 13900 |
| tctgcatacg ttcagggcac aggtccttta ccaggctctg ccccaggtct | 13950 |
| ttcggagagc aggtgtcttt cgcattcctg actctgggga acctctagcc | 14000 |
| ctgccacatg gggtttgtta tggggcaggg gcacctgtgc cttcccacc | 14050 |
| acggggcttg gggatttggt gctgccattg ccctccctcg taggtggccc | 14100 |
| tagggggggtc cctccgcctc cgtttcctca tccagaaacc ggcagtgacc | 14150 |
| atcaccacca ttgttgtcac ctagctccag ctcaaggtcc ctgctgaagg | 14200 |
| tcggagagct tggcatggcc ccgttttgtcc atgctagggc tgggaagacc | 14250 |
| aaggctcagg tgaggcctct gcccagtgcc tggcactcct tcttgcccca | 14300 |
| tttttccacc cagggtggct cccgactact tctggtagcc tcggggacag | 14350 |
| ttgaggtgga caggctggcg tcaccccat ttccggctgt ccctcccacc | 14400 |
| ccctcctggc ccagctgttc tgccctatta aaagtcacat gggccctcgg | 14450 |
| gtccttcctg gtgttggccc aggctctttc aggccctgca ggccaggacc | 14500 |
| agccttccct gcaaccctcg gcagaggcct ggggccgggg cttgtctagg | 14550 |
| ggcagcctcc ccatacggcc ctggagtctg aacagaagcc ccttcccaga | 14600 |
| gcacagcaag aagctgcaac gtggcctgaa gtcccaccat tagcaggttt | 14650 |
| ggggtttagg ctgagctttg ccatcactac ctttctgtta ggacggtatg | 14700 |
| cccattagat gggatcatcc cctcagcgcc caggctagag gagggtggt | 14750 |
| ccctgcccag ccagggaggg ctgggggtgg atgggcctct acagagcagc | 14800 |
| ttccgagcca ggcacggttc catgatcagc tctgttttat agaggggac | 14850 |
| actgaggaac cgggagcctg gggaccttcc agtggcccca cagctcctgt | 14900 |
| ggctgagtca gggtttgtca ccaggcctct gtggggatga ggctccccca | 14950 |
| tccacctgcc ccactctgtc ctggaacagc tctcaaaacg gtctctggac | 15000 |

| | |
|---|---|
| cacagtttca aaacaaaata agcaatgttt tcaaaggccc tggaggaagc | 15050 |
| cagagttacc acggcaactc tcggcctcgc cacctcctcc cgccaggctg | 15100 |
| catctggagc cagctcagga gggcagcagg gtgaggacag ccaggctctc | 15150 |
| tggggccacc ccccagcccc cacccttcct gcctctcctg cactgtccac | 15200 |
| ggccctccct gtgctcccac gggtataatg gcacagaag aaccaggagc | 15250 |
| tgtctgcccc tgcaggattc tggaagccag gggcccctgg cctccctggg | 15300 |
| gccttgtcat gtgaggggca cacgtggggt cccagctgcc acatggcttc | 15350 |
| cagcgctgcc cgcaggtgta tgttgggccc ttggtgactc taatgcacct | 15400 |
| tccactcggc acagaagagc ttcagtctgg ggcctgggcg ggggaagtag | 15450 |
| gctgccatcc tcgctaaacc aaagtgtgaa aattgagttg aaactcccat | 15500 |
| aggagggcag gaggcacagc tcctcagaag aaggtctgag aaaccacagc | 15550 |
| ccaggttgtt gtktcgggtg tgtggagaag gtgctctggc agtcctgcka | 15600 |
| caggggacc atcaacagcc cctttggggt gagagccccr tggctgctgg | 15650 |
| caccagcagc ccctatgagg cttattttat ttttgagaca gggtcttgct | 15700 |
| ctgtcaccga ggctggagtg cagtggcaca atcataactc actgtagcct | 15750 |
| caacctcctg agctcaagcg atcctcctgc ctcagcctcc aaaggtgctg | 15800 |
| ggattacagg cgcttgctac cacgcccagc cccctctggc cttattgttt | 15850 |
| gccaggccca gctcaggtcc cggaggaggg gagacaggag tgtgagggaa | 15900 |
| aggggaaga ggtatagagc ccccagctcc tccacccacc cgaaccctca | 15950 |
| ccgaggccct agaccctaga ccggcctgac cggggggtcc tcaggccggg | 16000 |
| gacttgggtg caggccatgg tgctggggcc tgaagctcac gctctgctga | 16050 |
| gcacagcccc ctgcccaacc ccaccctggg gccctgcttc cctggccagg | 16100 |
| gccattggaa caggagtggg gctgtccagg tggtgttctt gggtccagcc | 16150 |
| ctcagtttct cttctgcagt tgaccggcag ccctgcatct gtggtggggt | 16200 |
| cggcgcctgg tgctggtgag gcaaggcctc agctgctggg acaggacctg | 16250 |
| cctggcaccc agctggtggc agagccaagc attccgactc agctctggga | 16300 |
| gcagctgcct tctgggctgg cattctccgc caggggggtt gtgccctcgt | 16350 |
| ggccccccc gggtgcctcc tcacctggct gatttcatct cctgtccccc | 16400 |
| tgcctcctcc tccaggaagc ccccagggcc tggccctcct tgagagtggc | 16450 |
| atggaggagg aagaagactc gcccaggccc atgggagttg gatggtggcc | 16500 |
| gcacttgtgg ggccctgacc ccataggctt cttcagcacg ccctggcctg | 16550 |
| ggtgatccct gcctgagggc tgtgcacggc tcatctgcca gaccagattt | 16600 |
| taggggattc ttgtactgtc ctcctggagc agcaggggg aaagcctgac | 16650 |
| ccacccagac tgtccagcaa caagggcctc ctgctgtggg ccagggaccc | 16700 |
| tggaactgac caattgtgtc ctaggacgc agagtcccca ggctgctaga | 16750 |
| gggctgtggg gccctgtttc atgcctgaag caggaagaaa ccccaggaga | 16800 |
| ggtctgaagg ggaccagcc cccacccgt ctagcaggga ggagcctctg | 16850 |
| caagaggccg aggggtgctg aagtggagga ggatagaggc agcaggactc | 16900 |
| agggtcactg gtcatttatg gggatcacac ggctgcagtg tgccctgcat | 16950 |
| ggtgctaggc accagggaca gcagaggaca agcctgtgtc ctctcccacc | 17000 |

```
accagagggc tgggcactgc ccctagggag agaggggggcc ttggtgtgtg    17050
cagagggggg cctggggcac gtgcctggcc tggtcagatg atcagagtgg    17100
gctgggctgg gcctggtctg ggcccagtc tcaagggcag accccacctg     17150
gctagagttg attgtgtgca caccggatga cccggcgttg aaggcctctc    17200
ctctctgtga gcctcatccc cacctgccag actcccagca cagcctgctt    17250
cctgccccag ctgctgagcg acagcgctgg gccggcttct kmgcgccct     17300
tcccccagcc catcttggaa accacagcag ygtccttcct cccaagtccc    17350
ttcccagggc tgacatccca cagcagggat gtatcccaca aaccccgcag    17400
gccctggtgc ctacagcttg gcctggtaac atcaaatcct accctctcct    17450
cctggcagca aagatggggt gccccacccc cagagttctc agcaccccca    17500
gacagaagca gtcccccagc gacctcagaa ctcttggggc gctgccacac    17550
ccttgcagga gggggcagtg ttcctgggat gctcaggtcc tggtatcacc    17600
tctggccaga tacggaaggt gaaactacag ggcatccaat tcaccttgaa    17650
cttcagataa acaccagatt attttttttgt atgtcccgtg caatatttgg    17700
gacacactta ccctaaagaa gtattctgtt ttcatctgag aggcagattt    17750
aaccggcgtc ccgtgtcttc ctggcagtcc tgccctggag tcacactcca    17800
caggtcagg gcagggccag gctccaagta gatggcggcc aaagcacccg     17850
ccccatgctc ctgactcccg ggctcttca gggcattgcg aaaaccagca     17900
gcagagctga cacctggtcc ctgctcggga gccagcaagg caggaggctg    17950
cttaggcctt gcgtgtgggg tgggcgcact ccctgctgca gtgctcttcg    18000
tacatgtgac actgttcccg ctcttttccca gctggctgga ggcgtgatcc   18050
tgggtgtggc cctgtggctc cgccatgacc cgcagaccac caacctcctg    18100
tatctggagc tgggagacaa gcccgcgccc aacaccttct atgtaggtga    18150
gtgcacatgt ggccgcagac gcattcaggg agggcttcta ggaggaggca    18200
ggtcctagcc ttttggatgg ggacatggag ggtgaaagac agtcgggcat    18250
ggcgtgtccg ggcagggagg cggccctgga aagggctctg ggcacaaggg    18300
ttgagatgga ggtgggcctg tggcctgctg gcccttctgg tctgagccag    18350
ggcaggggt ggcagctagg cctgggcagg gactgtgtgg agaccttgct     18400
tattttaagt gtgggttat tcggggagg gctccctgag aagggtgggg      18450
ctggatgcct gggccacaca gagcagccga ggcagctggc gctgtggagc    18500
ccgggaggga gggagggatg gagctcaagg gatggaaccc agtgaggggt    18550
ggagacgggg caggggaggg gtggagaggg gtggagacgc cccagaggcg    18600
gtgtgactca gctgcccctg caggcagctg caccttgctg ccttattagg    18650
ctgcgtgtgg gggactgggc tgccctccct gccccagga gcaggagcag     18700
gagtgatgga ggaggaggag gggagggggca aggccaggag gaggaggagg   18750
gccatctcac tgtgcagaga gcagcaccct tcctcctggt gccccctggca   18800
gggctggtgc tggtggggct ctgggagcat tgttgagat gcttctggcc     18850
ttgaaaggag gccccctggga tggctctgtt gccctcacag gctgagggt    18900
gggtgaggtg ggcagcctgt gtgtccccag tcctcagggc ttccctcagc    18950
```

```
cggcaggtgc ccccaggcct ggagctgcag ggccaggccc cctgccagtt    19000
acggaggctg cttggcttgg ttgctgaacc agggcccag gaggccgaaa    19050
tagccccaca cctgcgccgt cccacctctt tgtccagtca ccccagggcc    19100
aggtgagggc cctggccaca cagcgtgccc gttccttctt ccccatgccc    19150
cgctcatggg tcagagggcc ggtgctgggg tccagatggt gtcaacaggg    19200
atggtccctg tcctccccag agacagaagc ctgtggccca cggagggttt    19250
ctgggcccag ccgatcctag ggagggtccc atggccctgc ccataggttc    19300
ctggcctctc tcggggccgt ggtgccctca caggtggtgt caggaaggac    19350
gggaaaggct gcttgtccca ggggctcatg tggagaccac ccctgcacg    19400
cagctggggc gctcctgcct gtgtcctcag aagcactcgg cttagctttg    19450
cccatgtgcc tgggctgtgg gtggcagagc ccggccagca tcctccgatc    19500
tccaagggtg catctctact ggaggcccct cctgggcctc ttgctccccg    19550
cttcccagat cattaggata tttggggtcc agaagggcct cccagccatc    19600
ctgggccttg tcctccgggg ccaccagtcc agccagtgac aaccacagca    19650
tccccggcct ggaacgaggc tgccccagc acgttcctcg tactcctgtc    19700
cagggacagg aggggctgcc cctgccaccg agtccccttc tccaggacct    19750
ggggcctgtg ggtgtgaggc aggtgttctt ggaagggtc actctccagg    19800
cacccggcgg ccaaggcttg tggctggagc agctcccgct gtggggtcgg    19850
cgtcgggccc cgtgtggccg agaggagct gaagggtcac ttagcttcgg    19900
gctggggcga ggacagggga caccccagag aggtatgcca ggcctccttc    19950
ctgcgcccca ctctcggcag aagcagaggt cacaggctgt gctgaggccc    20000
catggtgctg cccccatgat gccagggtga ggctggcgtt ggaagcaggt    20050
gtctgacctg catggtgtca ccgtggccac atcagagctc cagccccaga    20100
gccgcccacc ctcggtcctt ggctgtggtt tccctgggct ggaggagcct    20150
gccgttgtgt tggccacacg accacaggac ctgccacccc cgacgtgggc    20200
tctgcctggg cccccactgg acagggaccc cttggagctc ctctggccac    20250
caagtcctcg cccattccag aatcggcctt ctggagcctc ttgctgtccc    20300
tgatgcgggc tgggccttgc caagggcttt ttttcctgcg ccgggaacag    20350
ggtggatttg ctgggctcac tccctcaga gacgctgcgg gtgcgtggg    20400
ttaggcccaa gggcgttaag agaggaggct ggggtgggc tggggcctgg    20450
caggggtct ggcagccctg gcctcccac ctcctgtcag gaccaaaaaa    20500
ggcaacgcgc ctctcctgac ctgtaccccg gagtgaaccc aaccttgcaa    20550
cccaggagtg tcagggcctg aggggaggga gacctggctc ctgggtgccg    20600
tgcccgtaag gaggtggcca cctgcagggc attcctggca gaggcttcat    20650
ctggccaggt aggaggctgg gtggccgagc cccaaatctg ggtgtgttct    20700
ctgcctggcg gtgggtcctg ccccaggcac cttctcctct gggctggctg    20750
ggcagggaca atgggcctgg ctgcgaggag ggggcctggg ctgccttctg    20800
cattgcctcg gtgacgggag atgcccctg cctgctgagg gataggggag    20850
tgggcaggca gtgagagaca ctgacagctg tcccgcgggt acagggccct    20900
gtctgggtgg ccaggcccat gtctcggcc cacagtgcgc cccccaccct    20950
```

-continued

| | |
|---|---|
| tggacggcgc cttctccctc cccaggtgca tgctgcccag ccagggagcg | 21000 |
| tgggggagtt cgggagggct ggcctacacg ccctggtcca gctgtcccag | 21050 |
| gtggggtgct gggcttcagc cctcagccca gggcctagga agccaacttg | 21100 |
| atcctcccca cacagcagcc aggttcaaat gcaggtcccg taacggaagt | 21150 |
| gctgctgtgc agcccagatt gggggcagg agccagcagg gccccccac | 21200 |
| cctcttctcg caccacactg gggaggcagc attggttcca gttccggttc | 21250 |
| ctgggctgcc ctctcaaccc cggcctacag tggggcccac cctgtgcctt | 21300 |
| ctgatgccac tcccacccca cgccaagtcc cagaggcttt gggagcgggt | 21350 |
| gaaggcggtg ggtggcgggt ggcaggtgca ggcggtgggt ggtgggtgtg | 21400 |
| gcaggtggcg ggccccaccg caggtgtcat ccctgcgaag cacctgtcgc | 21450 |
| cagcactcag agcgctcatg aggtgccag tccccatgtg gcctccttag | 21500 |
| tctccgtcct gtgtcatgga agaggtaact gaggcacaga aaactcacca | 21550 |
| ggccaggctg ggatgtgagg tcccttgctg ctcatccctg gcagtcagca | 21600 |
| accctacatc ttcccagctg gcggcccgt ggtgggttcg gcacccagga | 21650 |
| ccctccgggg tcttgggctg tggcgagtgt gtaggcaccc acctggtgtc | 21700 |
| tctctcccg caaggcatct acatcctcat cgctgtgggc gctgtcatga | 21750 |
| tgttcgttgg cttcctgggc tgctacgggg ccatccagga atcccagtgc | 21800 |
| ctgctgggga cggtaaggca gggaggcggg cctgtgcctg gccggggag | 21850 |
| gggctggggg ctgcgtctgg ccctgaggag ggggcagagc tggtgctcag | 21900 |
| ggcggagcct agaattctgg gggaggtggc tcctgtgccc tgcttttccc | 21950 |
| gtttggtttt taaattaaat cccaccgtgc ttggtctcca tcgtggccag | 22000 |
| ttcctacgtg accgcttttc tttgtcaaaa aatagccaca aatataacag | 22050 |
| ggagcaagcc tcagctctga ggccagcctc ggcgtcccgg gcacaccgcc | 22100 |
| ccctgtggga agcccaggcc tggctgtgcc atccagggcc tggccagtcc | 22150 |
| aggaagaggg agcctatgcc cgtgtctcca gtgggggaaa ctgaggcaga | 22200 |
| tcccatggct cccccttccg tggggagcag gaacaagggg gtggggaaga | 22250 |
| tcagtcaggg gtcatgctgc tgcacacgcc tccctggggg ctgcagacat | 22300 |
| cctggactca ccagcctgtg accccaaacc acacgccccg ccccatccac | 22350 |
| cccatcctgt ggagcctggt gccgcgtggg gacatcctgg gctttgacgg | 22400 |
| ctcctccctg cgctgagttt tagcctctgt gccccagggc tccacacaag | 22450 |
| ccgctcactc ctggtcaggt cgtgggctgg tggctcccac tagcccctca | 22500 |
| cagacacgcc tgctgggcac ctgggtgtgt gtccttgggc cccgcctaca | 22550 |
| gcctgccctc tttcctccct ctggccactg cccggctcca gttcttcacc | 22600 |
| tgcctggtca tcctgtttgc ctgtgaggtg ccgccggca tctggggctt | 22650 |
| tgtcaacaag gaccaggtga gcctgggtgt gcagggacag ggtggggtgg | 22700 |
| gtgacggggg caccctcctc tcctgtcgcg ggtgggggtt gggctgactc | 22750 |
| atggcttgtg ggagctcttt gggctcttcc tgggtccac ttgccaggag | 22800 |
| gatctccagg ggctttatgg aggaggcagc attgggctg agcaccaggc | 22850 |
| cagcctcccg tgtcccagca ctcccggggc agctgagagt gcagagtcct | 22900 |

| | |
|---|---|
| tgtcctctgg ggtctagcct cgaagccacc ctgcccaggg agagcctggg | 22950 |
| aaaagtgcgt ccgcctgggg cggggcgggg tgggggcaag gagggggagg | 23000 |
| ttcccccctgt gcatgtgacc gcacccctcc cccagatcgc caaggatgtg | 23050 |
| aagcagttct atgaccaggc cctacagcag gccgtggtgg atgatgacgc | 23100 |
| caacaacgcc aaggctgtgg tgaagacctt ccacgagacg gtgcggcccc | 23150 |
| gggggggcgag ggcggggagc agggccccgg gaacccggcg gggtgtgtct | 23200 |
| cgtcctggat gaatcctgcc tacgcccaga cctcaggagc aggaggtgcc | 23250 |
| cttgggacct ccaggacccc tggtctcaac tggtcctcgg gtgggaacct | 23300 |
| agtgggccag ggtggcccag ggtgcggaaa gctctgagca gcgcagctga | 23350 |
| ggaggaagaa ggctggcccc tggatgcatt ctgcagtggg gagcgctgcg | 23400 |
| taccctggc cacctcccca tgggttccct agagccaccg tcccctggg | 23450 |
| cacatccagg gctgaccttg caccctgct ctctgcagct tgactgctgt | 23500 |
| ggctccagca cactgactgc tttgaccacc tcagtgctca agaacaattt | 23550 |
| gtgtccctcg ggcagcaaca tcatcagcaa cctcttcaag gtgcgcgagg | 23600 |
| ccggtggggc cgcgcctgac cccccgcatg tcccgcccct gggtggggtc | 23650 |
| ctaggggtgg gcaggtcaca cggcagcccc acagggagcg accacactgg | 23700 |
| gtggcatggc ccctgtcagg gctgctctgc tgggagggtt ggggtgggac | 23750 |
| cgcatctggc ccacgaggaa ggcaggcgcc ctgtgctgcg cattccgggt | 23800 |
| gaagaaggtg gaggctctgg ggggtgggaa ctcacctgca cccccagctc | 23850 |
| cacgtgtgca ctcgtgggtg tggacgcccc tgacagcctg tagctggcag | 23900 |
| ggcctgcagg ccatatagtg ccctgtggaa gtttcctgct gaggcctcag | 23950 |
| tggaagtcgt catcagtgat gctttagggg tctagtgaca ccaatgaccg | 24000 |
| tgatctcagt ggaaaagggc acagtgtgtc ccaggcattt cgcgtttatg | 24050 |
| ttaaaacggg tggaagatag caagccggca gaggccgggc cgctgcaccc | 24100 |
| gcctgttccg aggtgggtag ggggtggggg gctgttccca ggattcccct | 24150 |
| ctacgctttc tgtggtgacc acggattact gcgtgacaac gggaagccgg | 24200 |
| gagccgaggc ccggtccctg accacgcgtg cctggccacc cctgcaggag | 24250 |
| gactgccacc agaagatcga tgacctcttc tccgggaagc tgtacctcat | 24300 |
| cggcattgct gccatcgtgg tcgctgtgat catggtgagc gggcggggc | 24350 |
| ggagggcctg ctctctgggc tgcccccttcc gcggggcctt gtgctgactg | 24400 |
| cgccccccac caccctcctg cagatcttcg agatgatcct gagcatggtg | 24450 |
| ctgtgctgtg gcatccggaa cagctccgtg tactgaggcc ccgcagctct | 24500 |
| ggccacaggg acctctgcag tgcccctaa gtgacccgga cacttccgag | 24550 |
| ggggccatca ccgcctgtgt atataacgtt tccggtatta ctctgctaca | 24600 |
| cgtagccttt ttacttttgg ggttttgttt ttgttctgaa ctttcctgtt | 24650 |
| acctttcag ggctgacgtc acatgtaggt ggcgtgtatg agtggagacg | 24700 |
| ggcctgggtc ttggggactg gagggcaggg gtccttctgc cctggggtcc | 24750 |
| cagggtgctc tgcctgctca gccaggcctc tcctgggagc cactcgccca | 24800 |
| gagactcagc ttggccaact tggggggctg tgtccaccca gccgcccgt | 24850 |
| cctgtgggct gcacagctca ccttgttccc tcctgccccg gttcgagagc | 24900 |

```
cgagtctgtg ggcactctct gccttcatgc acctgtcctt tctaacacgt        24950
cgccttcaac tgtaatcaca acatcctgac tccgtcattt aataaagaag        25000
gaacatcagg catgctacca ggcctgtgca gtccctcagt gccagtggtg        25050
tctgagacct aggggttggc cggagggcag gggaatctga catcggtggg        25100
gcttggctct gtggactctg tggggtccag ggtgagggtg ggtgggtcgg        25150
gatccctggt gttcaccaaa ggagtcactc tgtaaaattt ggggagttat        25200
ttattctgag ccaaatatga gcaccggtgg cctgtgacac agccccaggt        25250
cctgagaact tgtgcccaag gcggtctggc tacttaattg tatacatttt        25300
agggacatag gacattgatc attacatcta agatgtacgt tggtttagtc        25350
ggaaaggtgg gacgatttga aggggaggga ctttcaggtc ataggcggat        25400
taaaagatgt tctgattaat aattggttga ttttatctaa agacctgaaa        25450
tcaatagaat ggactatctg ggttaagagg agttgtggag accaagatta        25500
ttatgcagat gaagccgcca gattgtaaat gtttcttatc agacttaaaa        25550
aggtaccaga atcttagtta attctctcct ggatcaggaa atagacctgg        25600
aaagggaggg ggattctcta tagaatgtag attttcccaa gagacagctt        25650
tgcagggcca tttcaaaata catcagagaa atatattttg gggtaaaata        25700
cttcggtttc tttcagggcc tgctgtcacg ttggtatctt attactacag        25750
agtctgtttt gtgagtctta aggtctttt attttttagac agagttttgc        25800 tcttgtcacc caggttggag tgcaatggcg tgatctcagc tcactgcagc        25850
ctcccctcca cctcccaggt tcaagcgatt ctcctgcctc agcctcctga        25900
gtagctggga caacaggcat gcaccacccc acccagctaa ttttgtattt        25950
ttagtagaga cggtgtttcg ccacggtggc caggctagtc tcgaactcct        26000
gacctcacgt gacacac                                           26017
```

METHOD FOR DETECTING A PROPENSITY OF AN INDIVIDUAL TO RESPOND EFFECTIVELY TO TREATMENT OF INTERFERON-α AND RIBAVIRIN COMBINED THERAPY

FIELD OF THE INVENTION

The present invention relates generally to HCV treatment, and more particularly to gene and genetic polymorphisms associated with treatment efficacy of interferon-α and ribavirin combined therapy on HCV patients.

BACKGROUND OF THE INVENTION

According to most recent World Health Organization (WHO) estimates, around 170–200 million individuals have chronic HCV infection worldwide. The HCV prevalence shows significant geographic variations and demographic variations within a geographic area. In Europe, and particularly in the Mediterranean countries, the prevalence of HCV infection increases in parallel with age, while in the United States it is most common in persons 30–49 years of age, see W. R. Kim, The burden of hepatitis C in the United States, Hepatology 36 (2002) S30–S34. The incidence of new infections with HCV is declining in the developed countries while the number of new cases is still increasing in the underdeveloped countries, largely due to the use of contaminated blood for transfusion. The major risk factor for HCV transmission has changed over time from blood transfusion related cases to injecting drug use in the Western world. The relative importance of other risk factors has not changed much over time. These include unsafe sex with multiple partners, occupational and perinatal exposures, nosocomial and iatrogenic infections, unsafe tattooing, piercing and acupuncture, see M. J. Alter, Prevention of spread of hepatitis C, Hepatology 36 (2002) S93–S98.

Hepatitis C is caused by a small RNA virus belonging to the flaviviridae family and has been recently classified as the only member of the genes *hepacivirus*, see B. Robertson, G. Myers, C. Howard, T. Brettin, J. Bukh, B. Gaschen, et al., Classification, nomenclature, and database development for hepatitis C virus (HCV) and related viruses: proposals for standardization, Arch Virol 143 (1998) 2493–2503. The HCV genome is a 9.6 Kb single-stranded RNA which encodes a single polypeptide of about 3000 amino acids, see M. Major, S. M. Feinstone, The molecular biology of hepatitis C, Hepatology 25 (1997) 1527–1538. This HCV polypeptide is cut post-translationally to generate several structural and non-structural proteins including two envelope glycoproteins (E1 and E2), the nucleopeptide protein (core-C) and several non-structural (from NS2 to NS5) proteins. Some of the viral proteins have been shown to involve in the pathogenesis of the liver disease and also in the development of resistance to interferon therapy. The HCV core proteins, either in its full-length or truncated forms, have been shown to provoke apoptosis of infected cells, see A. Ruggieri, T. Harada, Y. Matsuura, T. Miyamura, Sensitization to Fas-mediated apoptosis by hepatitis C virus core protein, Virology 229 (1997) 68–76, and thus might directly involved in the pathogenesis of liver disease, of cell proliferation and liver cancer development. The core proteins and NS5A have also been reported to interfere with cellular metabolism of lipids and with a direct effect on the development of steatosis, see G. Perlemuter, A. Sabile, P. Letteron, G. Vona, A. Topilco, Y. Chretien, et al., Hepatitis C virus core protein inhibits microsomal triglyceride transfer protein activity and very low density lipoprotein secretion: a model of viral-related steatosis, FASEB J 16 (2002) 185–194, which is a characteristic feature of hepatitis C, see L. Rubbia-Brandt, R. Quadri, K. Abid, E. Giostra, P. J. Male, G. Mentha, et al., Hepatocyte steatosis is a cytopathic effect of hepatitis C virus genotype 3, J Hepatol 33 (2000) 106–115. In addition, NS5A may contain an interferon sensitivity determining region (ISDR) capable of regulating the cellular response to interferon, see N. Enomoto, I. Sakuma, Y. Asahina, M. Kurosaki, T. Murakami, C. Yamamoto, et al., Mutations in the non-structural protein 5A gene and response to interferon in patients with chronic hepatitis C virus 1b infection, N Engl J. Med. 334 (1996) 77–81. This protein region can bind and inhibit protein kinase R (PKR), whose activity is pivotal for the development of intracellular antiviral state in response to interferon, see S. L. Tan, M. G. Katze, How hepatitis C virus counteracts the interferon response: the jury is still out on NS5A, Virology 284 (2001) 1–12.

There are six major different HCV genotypes and multiple subtypes. Genotypes 1a and 2b are most common in Europe and the United States, followed by genotypes 2 and 3. These four genotypes are also common in the rest of the world. On the other hand, the other genotypes are only common in particular geographic area, such as Egypt in the case of genotype 4, South Africa in the case of genotype 5, and Southeast Asia in the case of genotype 6. The viral genotype is important in terms of the treatment efficacy of antiviral therapy, see T. Poynard, P. Marcellin, S. S. Lee, et al., Randomized trial of interferon alpha 2b plus ribavrin for 48 weeks or for 24 weeks versus interferon alpha 2b plus placebo for 48 weeks for treatment of chronic infection with hepatitis C virus. Lancet 352 (1998) 1426–32, and J. G. McHutchison, S. C. Gordon, E. R. Schiff, et al., Interferon alpha-2b alone or in combination with ribavirin as initial treatment for chronic hepatitis C. N Engl J. Med. 339 (1998) 1485–92, with better responses associated with genotypes 2 and 3 than with genotype 1. Some of the HCV strains had been reported to have enhanced virulence, but the molecular determinants and mechanisms conferring this property remain elusive, see P. Farci, S. J. Munoz, A. Shimoda, et al., Experimental transmission of hepatitis C virus-associated fulminant hepatitis to a chimpazee. J Infect Dis 179 (1999) 1007–11. Furthermore, genetic variations within a region of NS5A have been deduced to associate with the treatment effectiveness of interferon therapy, as shown in isolates of Japanese subtype 1b, see N. Enomoto, I. Shakuma, Y. Asahina, et al., Mutation in the nonstructural protein 5A gene and response to interferon in patients with chronic hepatitis virus 1b infection. N Engl J. Med. 334 (1996) 77–81. However, this result could not be reproduced in European and American isolates of HCV 1, see R. T. Chung, A. Monto, J. L. Dienstag, L. M. Kaplan, Mutations in the NS5A region do not predict interferon-responsiveness in American patients infected with genotype 1b hepatitis C virus. J Med Virol 58 (1999) 353–8, and S. Zeuzem, J. H. Lee, W. K. Roth, Mutations in the non-structural 5A gene of European hepatitis C virus isolates and response to interferon alpha. Hepatology 25 (1997) 740–4.

The natural history of hepatitis C is very heterogeneous, it can either progress towards cirrhosis and its complications, though over a quite long period of time, or remain as benign and one-progressive chronic infection in the majority of the HCV carriers. The severity, progression, and outcome of hepatitis are influenced by several cofactors, see A. Alberti, L. Chemello, L. Benvegnu, Natural history of hepatitis C, J Hepatol 31 (Suppl 1) (1999) 17–24. Retrospective studies conducted in patients with hepatitis C observed for 10–30 years after infection indicate that 17–55% (mean 42%) developed cirrhosis, 1–23% developed HCC and 4–15% died of liver related causes. These figures are quite reduced in most prospective studies where over a follow-up period of 8–16 years after exposure 7–16% of the patients developed cirrhosis (mean 11%), 0.7–1.3% developed HCC and 1.3–3.7% died of liver related causes, see L. B. Seeff, Natural history of chronic hepatitis C, Hepatology 36 (2002) S35–S46. In a series of retrospective-prospective studies lasting 9–45 years, it was found that 0.3–15% of the developed cirrhosis, 0–1.9% HCC, and 0–2.8% died of liver related diseases. These investigations also revealed that many host and environmental factors can influence the course and outcome of chronic hepatitis C and account for the great heterogeneity of this disease. These differences are very well described by the quite different outcomes and rates of progression to cirrhosis seen when distinct cohort of patients were followed-up for a similar period of time (20–25 years) after infection. In adult patients, mainly males, infected at the age of 45–65 years with a large inoculum through blood transfusion in the pre-serologic era, 15–27% developed cirrhosis, see R. L. Koretz, H. Abbey, E. Coleman, G. Gitnick, NANB post-transfusion hepatitis: looking back on the second decade, Ann Intern Med 119 (1993) 110–115, F. Tremolada, C. Cassin, A. Alberti, C. Drago, A. Tagger, M. L. Ribero, G. Realdi, Long-term follow-up of NANB (type C) post-transfusion hepatitis, J Hepatol 16 (1992) 273–281, and A. M. Di Bisceglie, Z. D. Goodman, K. G. Ishak, J. H. Hoofnagle, J. J. Melpolder, H. J. Alter, Long-term clinical and histopathological follow-up of chronic post-transfusion hepatitis, Hepatology 14 (1991) 969–974, compared to 4% with community-acquired hepatitis C, see A. J. Rodger, S. Roberts, A. Lanigan, S. Bowden, N. Crofts, Assessment of long-term outcomes of community-acquired hepatitis C infection in a cohort with sera stored from 1971–1975, Hepatology 32 (2000) 582–587, 1% of young drug-addicts, see D. L. Thomas, J. Astemborski, R. M. Rai, F. A. Anania, M. Schaeffer, N. Galai, et al., The natural history of hepatitis C virus infection: host, viral and environmental factors, J Am Med Assoc 284 (2000) 450–456, 0.4–2% of young women contaminated by anti-D Ig preparations, see E. Kenny-Walsh, for the Irish Hepatology Research Group, Clinical outcome after hepatitis C infection from contaminated anti-D immune globulin, N Engl J Med 340 (1999) 1228–1233, and 0.3% of children with hepatitis C, see M. Wiese, F. Berr, M. Lafrenz, H. Porst, V. Olsen, Low frequency of cirrhosis in a hepatitis C (genotype 1b) single-source outbreak in Germany: a 20-year multicenter study, Hepatology 32 (2000) 91–96. These findings indicate that size and source of infection, age and gender are important variables affecting the course and outcome of chronic hepatitis C.

The treatment of patients with chronic HCV infection is based largely on consensus guidelines, see National Institutes of Health Consensus Development Conference Panel statement: management of hepatitis C. Hepatology 26 (1997) Suppl 1:2S–10S, and EASL International Consensus Conference on Hepatitis C: Paris, 26–28, Feb. 1999, consensus statement. J Hepatol 30 (1999) 956–961. The 1999 recommendations, see EASL International Consensus Conference on Hepatitis C: Paris, 26–28, Feb. 1999, consensus statement. J Hepatol 30 (1999) 956–961, suggest that naïve patients with the above-described indications and without contraindications to treatment with interferon or ribavirin should receive combination therapy. Treatment consists of 3 million U of interferon-α administered subsetaneously three times a week and 1200 mg of ribavirin orally per day for patients with weight greater than 75 kg and 1000 mg of ribavirin for those less than 75 kg. Usually, ribavirin is taken in divided doses, given in the morning and evening, and interferon is given before bedtime.

The efficiency of these therapies is usually and conventionally determined by measuring a biochemical response (normalization of alanine aminotransferase levels), but recently the introduction of assays for the detection of HCV RNA have allowed the assessment of virologic response (as defined by a negative result on a qualitative PCR assay for HCV RNA) as a criteria for successful therapy as well. Since responses to therapy may not be maintained after treatment is stopped, the success of clinical trials has been evaluated in terms of the response at the end of therapy (end-of-treatment response) and six months after the cessation of treatment (sustained treatment response). Patients with a sustained virologic response have a high probability of having a durable biochemical, virologic, and histologic response, see O. Reichard, H. Glaumann, A. Fryden, G. Norkrans, R. Wejstal, O. Weiland, Long-term follow-up of chronic hepatitis C patients with sustained virological response to alpha-interferon. J Hepatol 30 (1999) 783–787.

The rate of end-of-treatment response of HCV patients to interferon monotherapy was as high as 40 percent, but the rate of sustained response is less than half of this, see T. Poynard, P. Marcellin, S. S. Lee, et al. Randomised trial of interferon alpha2b plus ribavirin for 48 weeks or for 24 weeks versus interferon alpha2b plus placebo for 48 weeks for treatment of chronic infection with hepatitis C virus. Lancet 352 (1998) 1426–1432, and J. G. McHutchison, S. C. Gordon, E. R. Schiff, et al. Interferon alfa-2b alone or in combination with ribavirin as initital treatment for chronic hepatitis C. N Engl J Med 339 (1998) 1485–1492. This is especially true in persons infected with HCV genotype 1a or 1b, the most prevalent genotypes in the United States and western Europe. Two large, prospective trials, see T. Poynard, P. Marcellin, S. S. Lee, et al., Randomised trial of interferon alpha2b plus ribavirin for 48 weeks or for 24 weeks versus interferon alpha2b plus placebo for 48 weeks for treatment of chronic infection with hepatitis C virus. Lancet 352 (1998) 1426–1432, and J. G. McHutchison, S. C. Gordon, E. R. Schiff, et al., Interferon alfa-2b alone or in combination with ribavirin as initital treatment for chronic hepatitis C. N Engl J Med 339 (1998) 1485–1492, demonstrated that the combination of interferon-α and ribavirin significantly elevates the percentage of naive patients who have a sustained virologic response, from 16% to 40%. Also, both studies showed that the treatment regimens with optimal clinical outcome were associated with the viral genotype and pre-treatment viral load. For patients infected with HCV genotype 2 or 3 and in those with low viral loads before treatment, the response was maximal after 24 weeks of the treatment, whereas patients infected with genotype 1 and those with a high viral load before treatment required a course of 48 weeks for an optimal outcome. This finding led to the recommendation that the duration of treatment should be based on the HCV genotype and the pretreatment viral load, see EASL International Consensus Conference on Hepatitis C: Paris, 26–28, Feb. 1999, consensus statement. J Hepatol 30 (1999) 956–961. However, since tests for the quantification of HCV RNA are still not standardized, and since the viral load naturally fluctuates over time, the viral load is currently not routinely used for determining the treatment regimen.

Therapy of chronic hepatitis C has greatly improved in recent years with the use of interferon-α and ribavirin combined therapy. The therapy has been further improved more recently with the use of pegylated interferons (PEG-IFNs), again combined with ribavirin. The recent NIH Consensus Conference of the Management of Hepatitis C has concluded that on the basis of available data the highest response rates to antiviral therapy for the treatment of chronic hepatitis C have been achieved using the combination of PEG-IFNs and ribavirin, at least for patients infected with HCV-1 and such regimen has been therefore proposed as the new standard of therapy for chronic hepatitis, see C A. Alberti and L. Benvegnu, Management of hepatitis C, J. Hepatology 38 (2003) S104–S118.

Factors influencing the rate of sustained virological response include viral and host factors, as well as the pathogenesis state of the liver. The viral factors include viral genotype (types 1a, 2 and 3 are favorable to response), level of viraemia (less than 2 million copies/ml is favorable), and level of viral heterogeneity (degree of variability in E2/NS1 region of HCV correlates with response to IFN). The favorable host factors include younger age (less than 40) as well as female sex. The beneficial pathogenic factors are lower ALT and AST levels before treatment, absence of cirrhosis and low fibrotic histological scores, and lower hepatic iron content, see A. Alberti and L. Benvegnu, Management of hepatitis C, J. Hepatology 38 (2003) S104–S118, and G. M. Lauer and B. D. Walker, Hepatitis C virus infection, N Engl J Med 345 (2001) 41–52. In addition, due to the great extent of inter-individual variations in response to the treatment, it has been speculated that host genetic factors may also play an important role.

CD81 is a membrane bound protein composed of four transmembrane and two extracellular domains with a molecular weight of 26-kDa, see S. Levy, S. C. Todd, and H. T. Maecker, CD81 (TAPA-1): A molecule involved in signal transduction and cell adhesion in the immune system. Annu. Rev. Immunol. 16 (1998) 89–109. It is a member of the superfamily of proteins known as tetraspanins, see H. T. Maecker, S. C. Todd, and S. Levy, The tetraspanin superfamily: molecular facilitators. FASEB J. 11 (1997) 428–442. Most tetraspanins were originally identified as leukocyte antigens; however, it is now becoming evident that generally tetraspanins, particularly CD81, is expressed in many different cell types and involved in a variety of cellular functions including cell adhesion and migration, alteration of cell morphology, and activation state of a cell, see I. Tachibana and M. E. Hemler, Role of transmembrane 4 superfamily (TM4SF) proteins CD9 and CD81 in muscle cell fusion and myotube maintenance, J. Cell Biol. 146 (1999) 893–904. In the immune system, on the B cell CD81 forms a complex with CD21, CD19, and Leu13. Formation of this complex decreases the threshold for B cell activation through the B cell receptor by bridging Ag specific recognition and CD21-mediated complement recognition, see D. T. Fearon and R. H. Carter, The CD19/CR2/TAPA-1 complex of B lymphocytes: linking natural to acquired immunity. Annu. Rev. Immunol. 13 (1995) 127–149. On T cells CD81 associates with CD4 and CD8 and provides a costimulatory signal with CD3, see T. Imai, M. Kakizaki, M. Nishimura, and O. Yoshie, Molecular analyses if the association of CD4 with two members of the transmembrane 4 superfamily, CD81 and CD82. J. Immunol. 15 (1995) 1229–1239. It is also shown that expression of CD81 by T cells greatly enhances cognate T-B cell interactions and greatly amplifies Th2 polarized intracellular activation pathways, see J. Deng, R. H. Dekruyff, G. J. Freeman, D. T. Umetsu, and S. Levy, Critical role of CD81 in cognate T-B cell interactions leading to Th2 responses, Intl. Immunol. 14 (2002) 513–523.

Recently, it was shown that HCV particles bind CD81 and this binding is mediated by the interaction of the second extracellular loop of CD81 with HCV envelope 2 glycoprotien in vitro, see P. Pileri, Y. Uematsu, S. Campagnoli, G. Galli, F. Falugi, R. Petracca, A. J. Weiner, M. Houghton, D. Rosa, G. Grandi, and S. Abrignani, Binding of hepatitis C virus to CD81. Science 282 (1998) 938–941. Since the interaction between CD81 and E2 is sufficient for binding of whole HCV particle, it was postulated that CD81 may act as a receptor for the attachment and entrance of HCV into the cell, see M. Flint, C. Maidens, L. D. Loomis-Price, C. Shotton, J. Dubuisson, P. Monk, A. Higginbottom, S Levy, and J. A. McKeating, Characterization of hepatitis C virus E2 glycoprotein interaction with a putative cellular receptor CD81. J. Virol. 73 (1999) 6235–6244. However, until now there is no conclusive evidence to demonstrate the involvement of CD81 in the cellular uptake of HCV virions. More recently, it was showed that the protein level of membrane bound CD81 in isolated human peripheral blood cells and hepatocytes was significantly down-regulated by the treatment of interferon-α alone or combined with ribavirin, see B. Kronenberger, B. Ruster, R. Liez, S. Weber, A. Piier, J. H. Lee, W. K. Roth, and S. Zeuzem, Interferon alfa down-regulates CD81 in patients with chronic hepatitis C. Hepatology 33 (2001) 1518–1526. Also, levels of total CD81 protein of the PBLs of HCV-infected patients are significantly higher than those of the healthy subjects. Furthermore, cell surface-associated CD81 protein was lower 4 weeks after initiation of therapy in patients with an initial virologic response compared with initial virologic non-responders. Therefore, it is concluded that interferon-α and ribavirin regulate the expression of CD81 in vitro and in vivo. CD81 expression correlates with initial virologic response in patients with HCV infection. However, the detailed regulatory mechanism of CD 81 expression by interferon-α and ribavirin remains unclear. Moreover, the underlying reason that differentiates patients with different level of CD81 expression in response to therapy requires further studies at the genomic level, particularly for the sustained response of the therapy.

SUMMARY OF THE INVENTION

Accordingly, the present invention provides isolated polynucleotides that encode sequences for CD81 gene SEQ ID NO: 46, which is shown to be associated with treatment responsiveness of HCV patients to interferon-α and ribavirin combined therapy. The polynucleotides include polymorphisms associated with responsiveness of interferon-α and ribavirin and are useful as the probes in screening for HCV infected patients suitable for interferon-α and ribavirin combined therapy. The present invention also provides linkage disequilibrium structure of CD81 SEQ ID NO: 46, haplotype information and its use for prediction of potential responders. The present invention further provides methods for detecting polymorphisms in CD81 gene SEQ ID NO: 46 and its surrounding regions, and methods of detecting a propensity to response to the therapy of interferon-α and ribavirin, using the isolated polynucleotides of the present invention.

BRIEF DESCRIPTION OF THE DRAWINGS

These and other objects, features and advantages of the present invention will become apparent to those skilled in the art upon consideration of the following description of the preferred embodiments of the present invention taken in conjunction with the accompanying drawings, in which:

FIG. 1 shows Table 1 of the primers SEQ ID NO: 1–45 for SNP genotyping of CD81 SNPs SEQ ID NO: 46 with FP-TDI method.

FIG. 8 shows Table 2 of the distribution of CD81 SNPs in Chinese HCV infected patients;

FIG. 9 shows Table 3 of the association of SNP markers of CD81 gene SEQ ID NO: 46 and its flanking regions with treatment responsiveness of HCV patients to interferon-α and ribavirin combined therapy;

FIG. 10 shows Table 4 of the CD81-SNPrs800136 alleles SEQ ID NO: 46 and associated treatment response status;

FIG. 11 shows Table 5 of the CD81-SNPrs800137 alleles SEQ ID NO: 46 and associated treatment response status;

FIG. 12 shows Tables 6 and 7 of the CD81-SNPrs800334 alleles SEQ ID NO: 46 and genotypes and associated treatment response status;

FIG. 13 shows Tables 8 and 9 of the CD81-SNP-pos1989603 alleles SEQ ID NO: 46 and genotypes and associated treatment response status;

FIG. 14 shows Tables 10 and 11 of the CD81-SNPrs2522012 alleles SEQ ID NO: 46 and genotypes and associated treatment response status;

FIG. 15 shows Tables 12 and 13 of the CD81-SNPrs2522013 alleles SEQ ID NO: 46 and genotypes and associated treatment response status;

FIG. 16 shows Tables 14 and 15 of the CD81-SNPrs800335 alleles SEQ ID NO: 46 and genotypes and associated treatment response status;

FIG. 18 shows Table 16 of the CD81-SNPrs800136 and rs800137 haplotype and associated treatment response status; and FIG. 19 shows Table 17 of the CD81-SNPrs800334, pos1989603, rs2522012, rs2522013, rs800335 haplotypes and associated treatment response status.

DETAILED DESCRIPTION OF THE INVENTION

Figure 2:
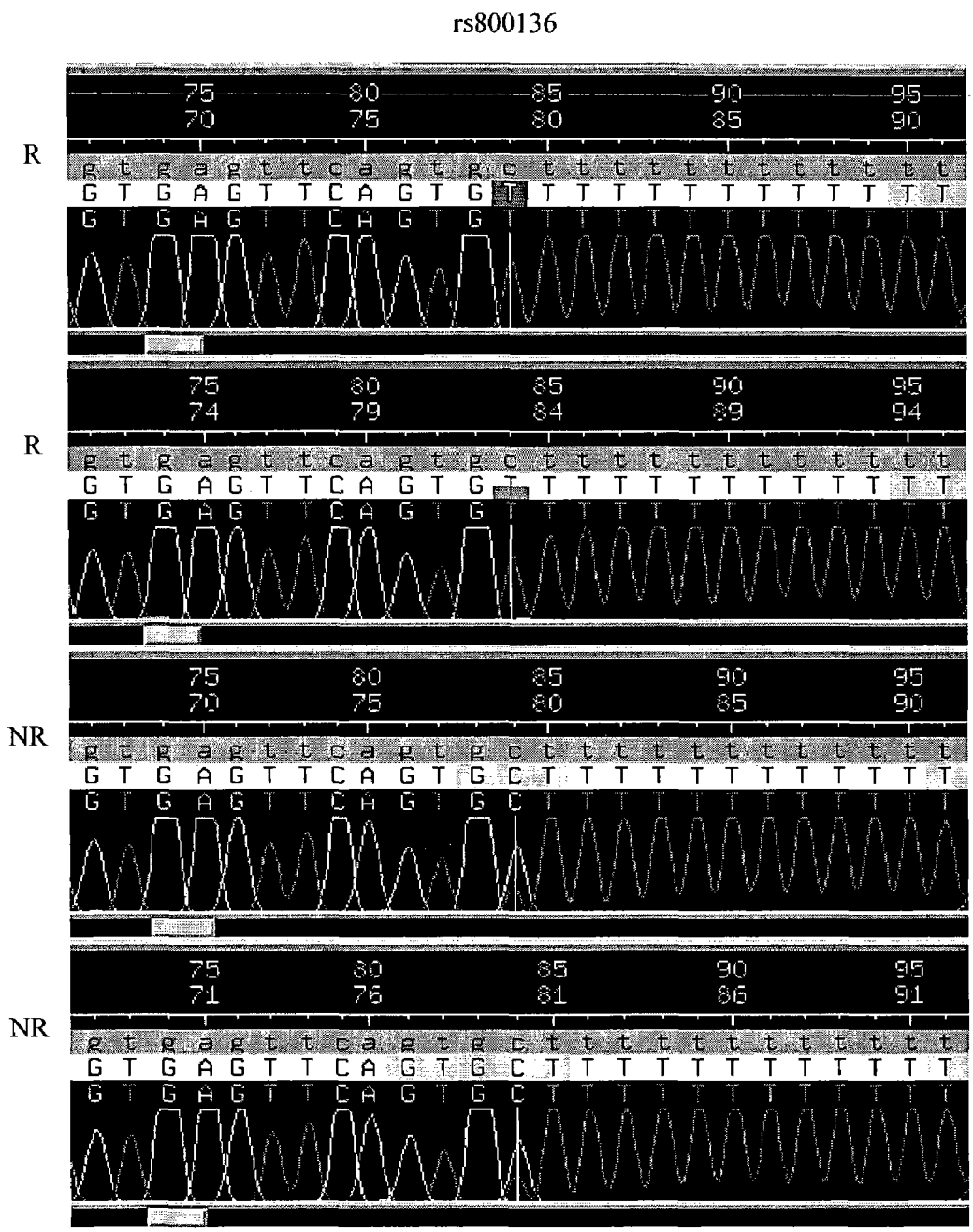
FIG. 2 shows the sequence traces of the responder and non-responder at and around rs800136.

It is directed to the investigation of the correlation of clinical responsiveness of HCV infected patients to interferon-α and ribavirin combined therapy with genetic polymorphisms in and surrounding the CD81 gene SEQ ID NO: 46. The results indicate that the treatment responsiveness is associated with the host genotype on CD81 gene SEQ ID NO: 46. The distribution of the allele and genotype of several SNPs upstream the CD81 gene SEQ ID NO: 46 is significantly different between the responder and non-responder groups. Further analysis of the linkage disequilibrium structure of the CD81 gene SEQ ID NO: 46 demonstrates that the significant SNPs are clustered in two distinct LD blocks. Moreover, distribution of haplotypes in these two blocks is also significantly different between the responder and non-responder groups. All of these results indicate that CD81 SEQ ID NO: 46 may directly involve in the treatment response pathway, and its genetic variations play an important role in determining the therapeutic outcome.

For reference, Appendix shows the nucleotide sequences of CD81 gene SEQ ID NO: 46 and its 5'-flanking region extended 5K upstream of exon 1 and the 3'-flanking region extended 1 kb downstream of the poly-A tail.

Methods and Materials

<Study Subjects>

Ninety two Chinese Han patients with chronic HCV infection were recruited at National Taiwan University Hospital. All patients' blood samples were Anti-HCV(+) and HCV RNA (+). Patients were excluded from receiving interferon therapy if they had any of the following criteria: neutrophil count <1,500 cells/mm$^3$, Hgb <12 g/dL in women or 13 g/dL in men, or platelet count <90,000 cells/mm$^3$, history of poorly controlled thyroid disease, and serum creatinine level >1.5 times the upper limit of normal at screening.

All patients received a combination therapy of ribavirin at a dose of 1200 mg per day and interferon-alpha (2a or 2b) at a dosage of 3–5 MU 3 times per week for 6 months, and were subsequently followed for treatment response via clinical, biochemical, and serologic markers for more than one year.

The definition of sustained responders to IFN and ribavirin combination treatment for chronic hepatitis C disease included patients with HCV RNA (+) to HCV RNA (−) conversion 6 months after treatment period. Patients with concurrent hepatitis B or D infection are excluded. Informed consent was obtained in writing from each patient. The study protocol conforms to the ethical guidelines of the 1975 Declaration of Helsinki as reflected by approval from the institutional review committee.

<Isolation of Genomic DNA>

Genomic DNA is isolated from blood sample using QIAamp DNA Blood kit according to the manufacture's instructions. The isolated genomic DNA is quality check by agarose gel electrophoresis analysis, quantity determined spectrophotometrically, and stored at −80° C. until use.

<Analysis of Single Nucleotide Polymorhpism>

SNP analysis was performed by either direct DNA sequencing or template-directed dye-terminator incorporation with fluorescence-polarization detection (FP-TDI) developed originally by Chen et al. (1999), see X. Chen, L. Levine, and P.-Y. Kwok, Fluorescence polarization in homogeneous nucleic acid analysis. Genome Res. 9 (1999) 492–8.

SNP Analysis by Direct DNA Sequencing

Multiplex Amplification of CD81 Fragment from Genomic DNA

The fragment of CD81 gene SEQ ID NO: 46 are amplified by a two-step PCR reaction. The initial amplification step is a multiplex PCR reaction containing 12 different pairs of PCR primers. The reaction mixture consists of 50 ng genomic DNA, 0.1 µM each of 12 pairs of primer, 0.25 mM dNTP mixture, 100 mM KCl, 20 mM Tris-HCl pH 8.3, 0.2% Triton X-100, and 5 mM MgCl$_2$, 10U of VioTaq DNA polymerase (VIOGENE) and 0.05U of pfu DNA polymerase (Stratagene) in a total volume of 100 μL reaction. The reaction is performed by a touchdown program with an initial denaturing at 94° C. for 4 min, 10 cycles of melting at 94° C. for 40 sec, annealing at 72° C. with 1° C. decrement per cycle for 40 sec, and extending at 72° C. for 1 min 30 sec; for the subsequent 25 cycles, the annealing temperature is 62° C. with the same conditions for denaturing and extending procedures, and one cycle of final extension at 72° C. for 10 min. Amplification is carried out using 2700 PCR machines (ABI) and the amplified products are purified by membrane ultra-filtration with MultiScreen PCR plate (Millipore) according to the manufacture's instruction. In the next step, specific 791 bp of CD81 SEQ ID NO: 46 product is amplified using the purified multiplex product as template is amplified from the simultaneously amplified products in a 78 to 72 touchdown program as described previously in 1 fold of PCR buffer. U.S. patent application Ser. No. 10/446,940 is also attached hereto for more detail to perform a two-step PCR reaction with touchdown programs.

Sequencing PCR Products Using Dye-Labeled Terminators

Each amplified and purified reaction product is divided into 96 sequencing reactions. The sequencing reaction is performed in a PCR machine with each reaction mixture consisting of PCR product, Big Dye Terminator Ready-Reaction-Premix and 10 pmol of sequencing primer. Reaction is subjected to 28 cycles at 94° C. for 30 sec, 48° C. for 30 sec, and 58° C. for 2 min. Reaction product is purified by ethanol precipitation, re-suspended in ultra-pure water, and loaded on an ABI 3700 capillary sequencer.

Sequence Analysis and Allele Calling

DNA sequence data and track are collected by ABI DNA Sequence Analyzer. Base calling is performed with Phred and sequencing assembled by Phrad. For ensuring the data quality only bases with Q value greater than 20 are analyzed further. PolyPhred is used for the initial identification of potential SNP sites. SNP sites identified are verified manually by three experienced researchers independently, and those scored by at least two researchers are deemed as true SNPs. Similarly, genotype of each tested individual is initially determined by the computer software and confirmed manually as for the identification of SNP site.

The work flow for SNP genotyping by TDI-FP is as follow: (1) primer design, (2) PCR amplification, (3) excess PCR primer and dNTP degradation, (4) single-base extension, and (5) FP measurement.

(1) Primer Design

Four primers are designed for each SNP site, two for PCR amplification of the DNA fragment containing the SNP site and two for TDI reaction. Primer 3 is employed to design the PCR primers. The PCR primers are designed to have a melting temperature between 54° C. to 56° C. The TDI primers are designed by a program, developed originally by Vieux et al., see E. F. Vieux, P.-Y. Kwok, R. D. Miller, Primer design for PCR and sequencing in high-throughput analysis of SNPs. Biotechniques. (2002) Suppl: 28–30, 32., and modified in house by our bioinformatics group, to have melting temperature between 50° C. to 55° C. and lengths between 20 to 30 bases (about 10,000 Da). Primers SEQ ID NO: 1–45 used for genotyping of SNPs of CD81 SEQ ID NO: 46 in this study are listed in Table 1 of FIG. 1.

(2) PCR Amplification

Human genomic DNA (5 ng) is amplified in a 10 μl reaction mixtures containing 1×PCR buffer (Applied Bio-systems), 2.5 mM MgCl$_2$, 50 μM dNTP, 0.1 μM each of forward and reverse primers, and 0.2 U AmpliTaq Gold DNA polymerase. The reaction mixture is held at 95° C. for 10 minutes for activation of AmpliTaq Gold DNA polymerase, followed by 35 amplification cycles. Each cycle consists of denaturation at 95° C. for 10 seconds, primer annealing at 55° C. for 20 seconds, and primer extension at 72° C. for 30 seconds. At the end of the thermal cycling, the reaction is held at 72° C. for 10 minutes for final primer extension and then incubated at 4° C. until use.

(3) Excess PCR Primer and dNTP Degradation

After completion of the PCR reaction, a 2-μl PCR Clean-Up reagent is added to 5 μl of the PCR reaction mixture. The PCR Clean-Up reagent contains 1 U shrimp alkaline phosphatase, and 1 U *E. coli* exonuclease I in shrimp alkaline phosphatase buffer (25 mM Tris-HCl, pH 8.5 and 2.5 mM MgCl2). The degradation reaction is performed at 37° C. for one hour followed by an incubation at 80° C. for 15 minutes for inactivation of the enzymatic activity.

(4) Single-Base Extension

To the Exo-SAP enzymatic treated PCR product (7 μl), 13 μl of the TDI reaction cocktail (AcycloPrime-FP Mix, Perkin Elmer) is added. The cocktail consists of components to give the reaction at the final concentrations of 1× reaction buffer (Perkin Elmer), 0.25 M SNP primer, 1 μl Acyclo Terminator Mix (Perkin Elmer), and 0.25 U AcycloPol DNA polymerase (Perkin Elmer). The reaction is incubated at 95° C. for 2 minutes followed by 25 to 50 cycles of 95° C. for 15 seconds and 55° C. for 30 seconds. At the end of the reaction, the samples are held at 4° C.

(5) FP Measurement

FP measurement is conducted on a Perkin Elmer fluorescence reader (Victor$^2$). FP value is defined by the formula $$p=(Ivv-Ivh)/(Ivv+Ivh), \quad [\text{Eq.1}]$$

where Ivv is the emission intensity measured when the excitation and emission polarized filters are parallel and Ivh is the emission intensity measured when these filters are perpendicular. The measurements are mathematically transformed to the expression of millipolarization $$mP=1000\times(Ivv-(G\times Ivh))/(Ivv+(G\times Ivh)), \quad [\text{Eq.2}]$$

where G is a gating factor near the value of one used to adjust for slight differences in the two optical paths used. G is estimated for each of the four dyes using an assumed mP value for the dye of 30 mP and measured values for Ivv and Ivh.

Determination of Genotype

The identification of the genotype of each sample is assisted by the allele calling program SNP Scorer provided by the manufacturer. In brief, the mP values of the two dyes, representing one of the two possible alleles, are plotted on an abscissa. A data clustering algorithm is used for classification of the data points into four separate groups. The genotype of each sample is assigned dependent on the group it belongs to.

Figure 3:
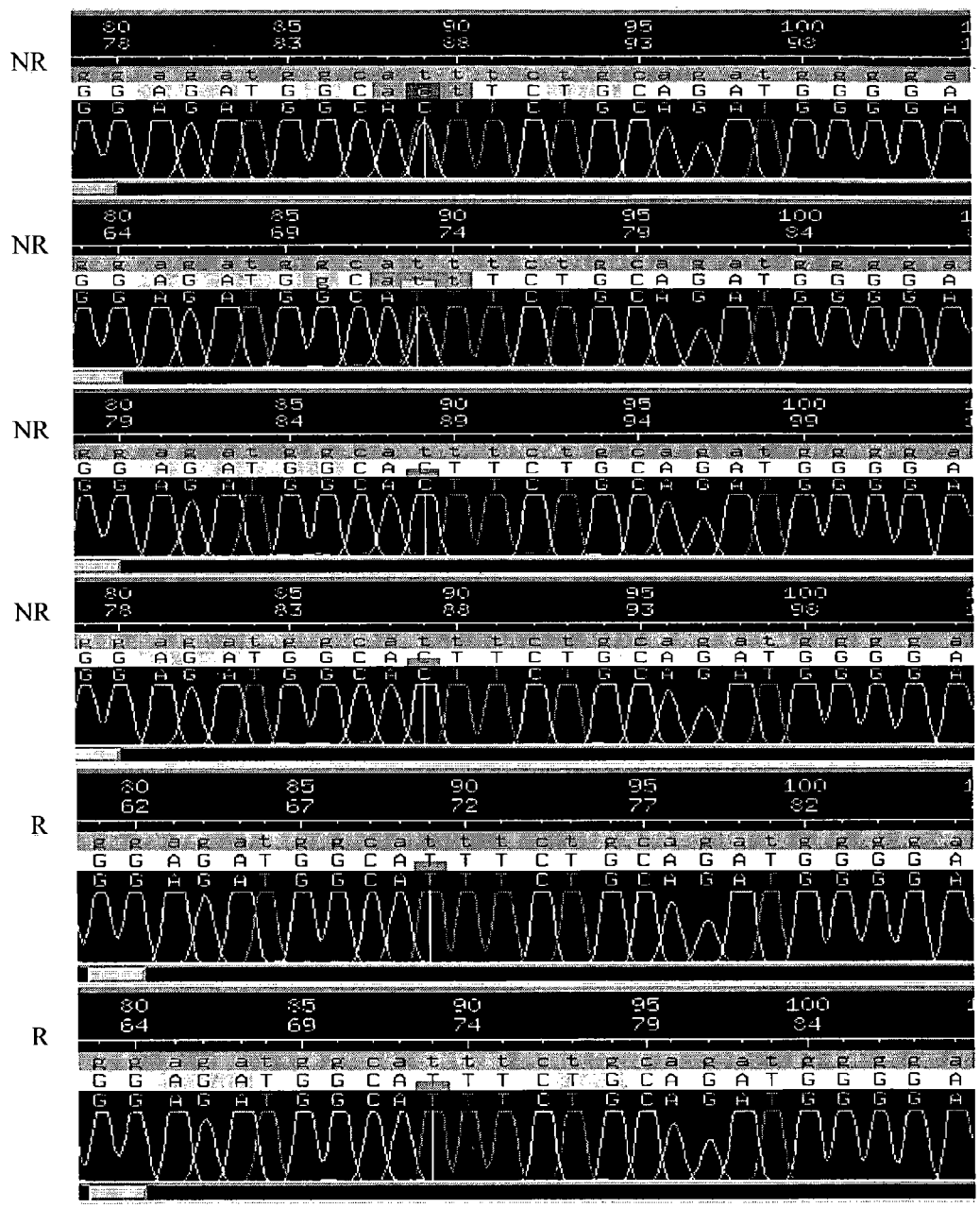
FIG. 3 shows the sequence traces of the responder and non-responder at and around rs800137.
Figure 4:
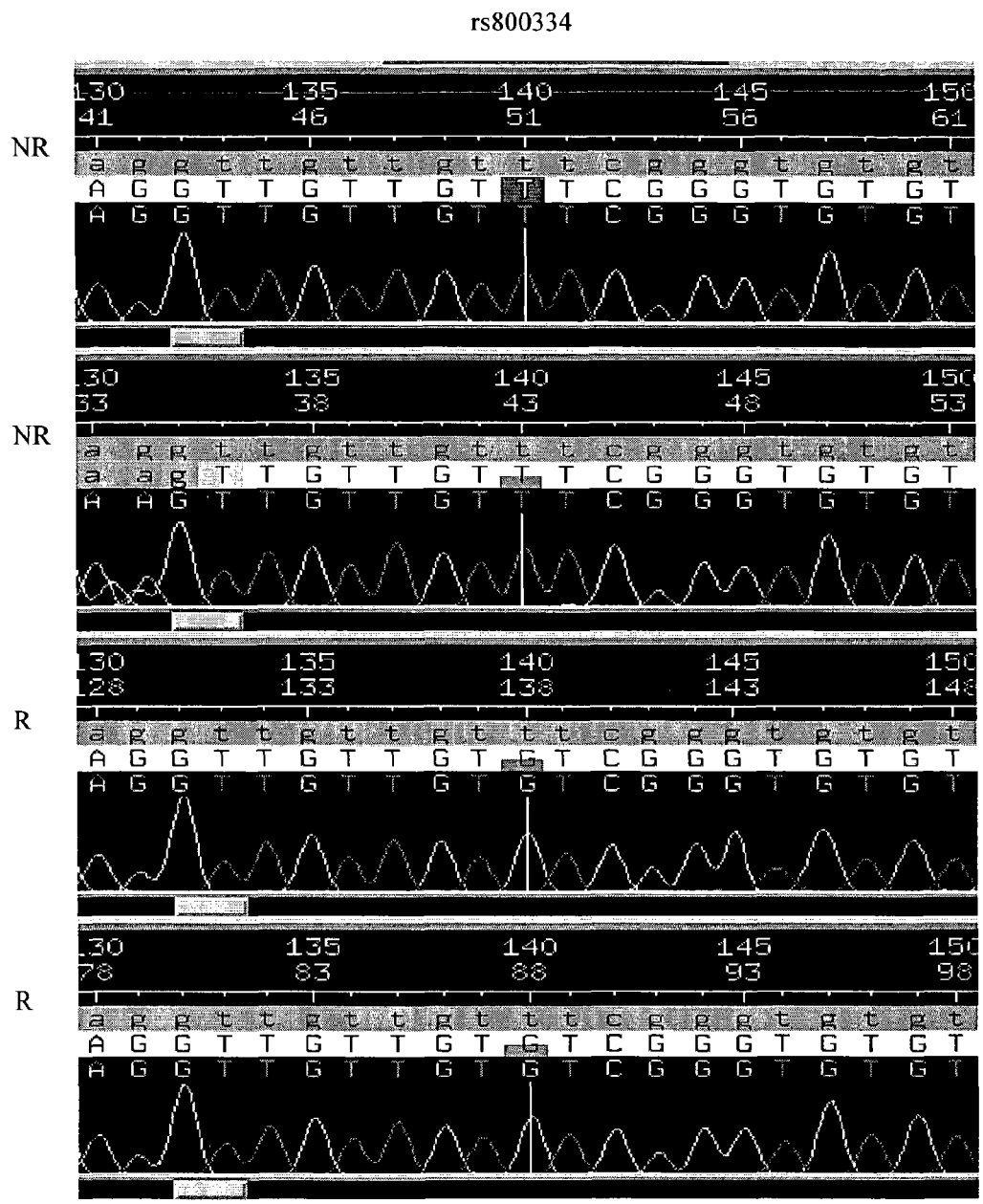
FIG. 4 shows the sequence traces of the responder and non-responder at and around rs800334.
Figure 5:
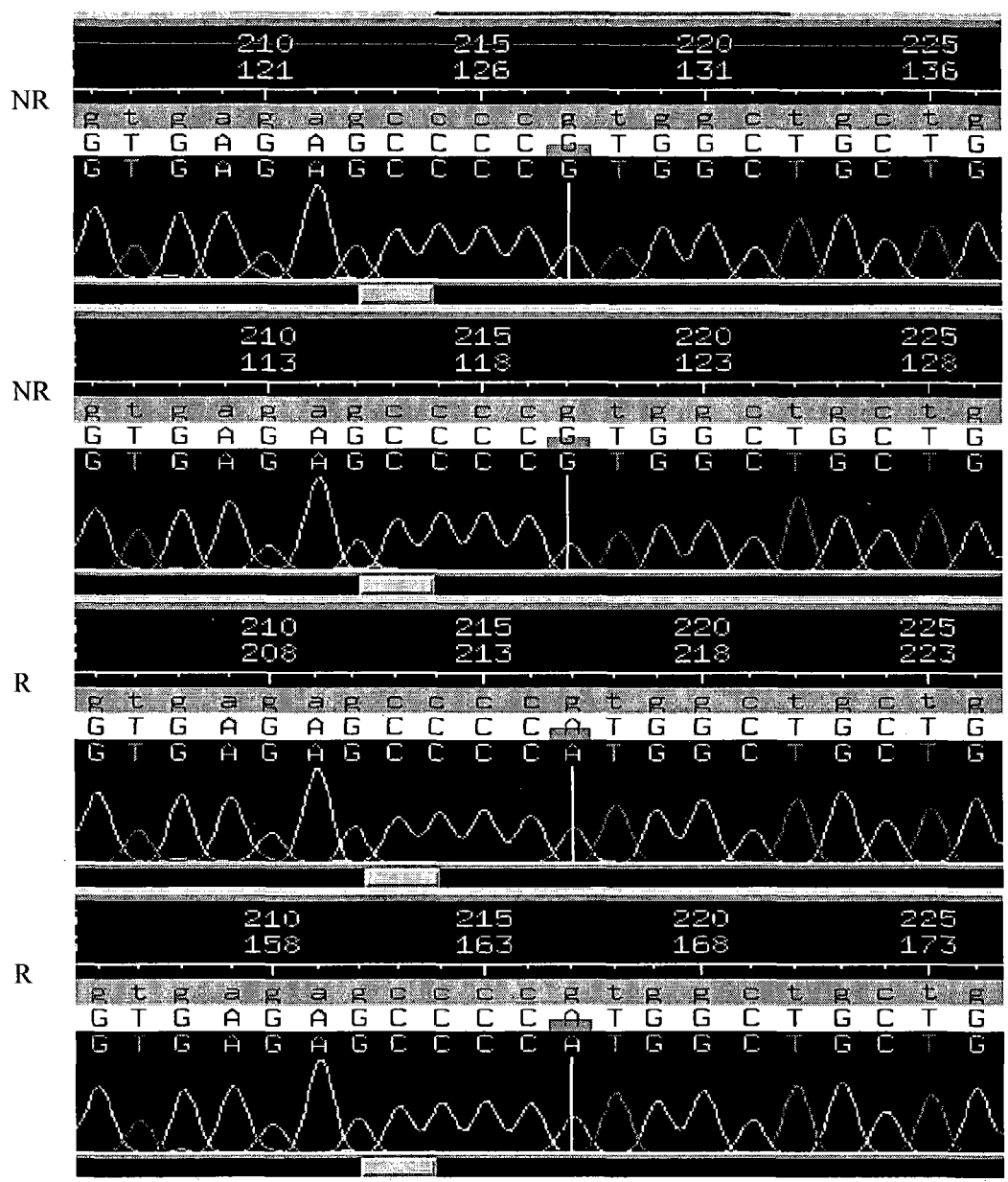
FIG. 5 shows the sequence traces of the responder and non-responder at and around pos1989603.
Figure 6:
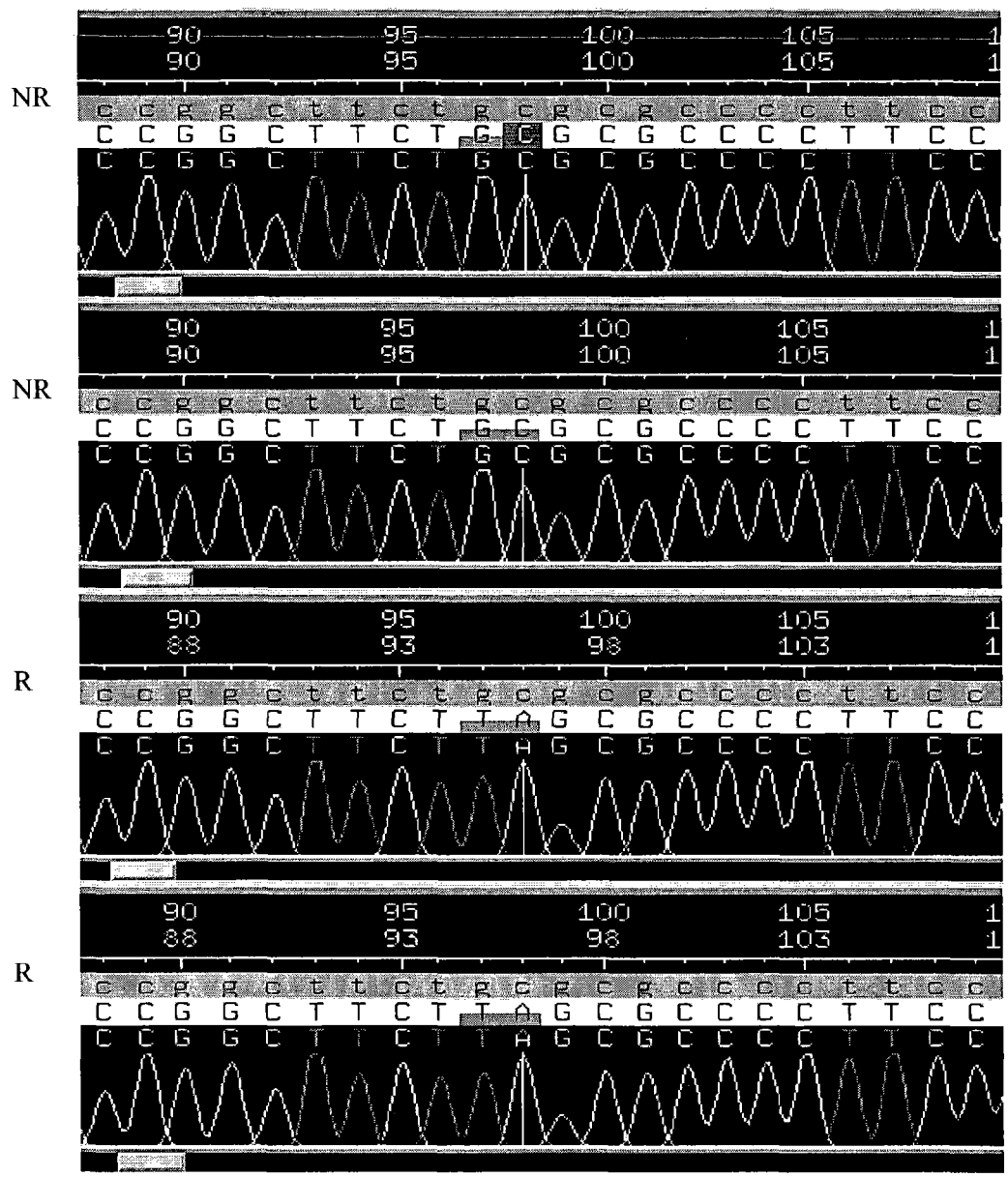
FIG. 6 shows the sequence traces of the responder and non-responder at and around rs8002522012 and rs8002522013.
Figure 7:
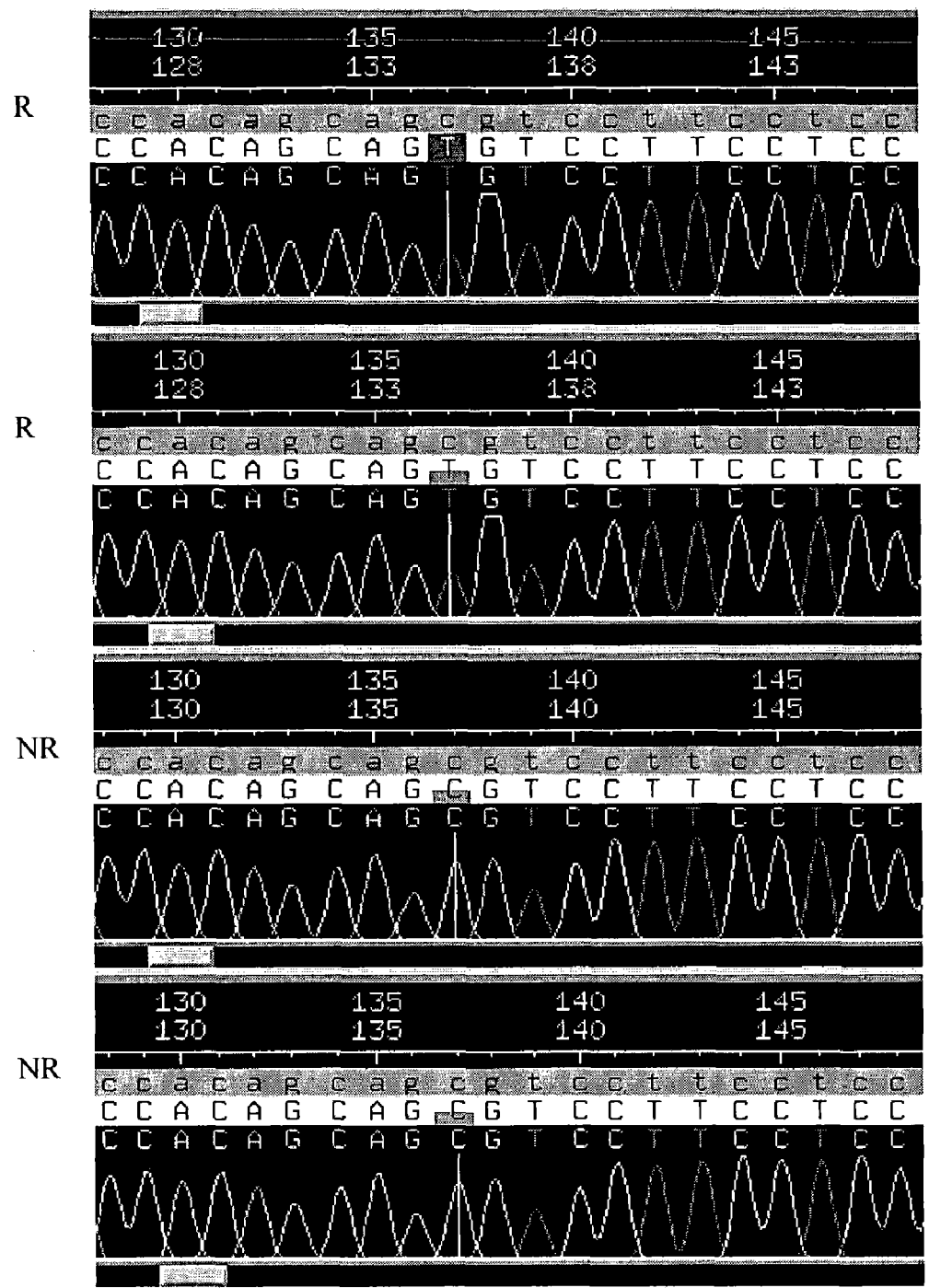
FIG. 7 shows the sequence traces of the responder and non-responder at and around rs800335.

FIGS. 2–7 show the sequence traces of the responder and non-responder at and around various CD81-SNP alleles SEQ ID NO: 46, respectively. FIG. 2 shows the sequence traces of the responder and non-responder at and around rs800136. FIG. 3 shows the sequence traces of the responder and non-responder at and around rs800137. FIG. 4 shows the sequence traces of the responder and non-responder at and around rs800334. FIG. 5 shows the sequence traces of the responder and non-responder at and around pos1989603. FIG. 6 shows the sequence traces of the responder and non-responder at and around rs8002522012 and rs8002522013. FIG. 7 shows the sequence traces of the responder and non-responder at and around rs800335.

Estimation of Haplotypes and Frequencies

Haplotypes and their frequencies are estimated on the basis of unphased genotype data, by the computer program PHASE. Described in the work of Stephens et al. (2001), PHASE uses a Bayesian algorithm that regards the unknown haplotypes as unobserved random quantities and aims to evaluate their frequencies and conditional distribution of multilocus haplotypes in diploid populations.

Statistical Analysis of Linkage Disequilibrium

Initial LD analysis is computed by performance of pair-wise comparisons for all SNP loci. Significance levels are determined by the $\chi^2$ test. SNPs having a minor-allele frequency less than 0.05 are excluded from LD analysis for the corresponding 2×2 table. Several widely used LD statistics of linkage disequilibrium are also computed: D, D' and $r^2$. For two loci $L_1$ and $L_2$, each with two alleles 1 and 2, let $p_i$ be the frequency of allele 1 and $q_i=1-p_i$ be the frequency of allele 2, at locus i (i=1, 2). Let $p_{11}$ be the frequency of the 11 haplotype and in general let $p_{jk}$ be the frequency of the jk haplotype. The coefficient of disequilibrium, D, is the difference between the observed haplotype frequency and the frequency expected under statistical independence: $D=p_{11}-p_1 p_2$. The labeling of the alleles may affect the sign of D, but not its absolute value. The relative disequilibrium D' ranged from 1 to −1, is obtained by dividing D by its possible maximal possible (absolute) value $(D=D/|D|_{max}$, where $|D|_{max}=\max(p_1p_2, q_1q_2)$ if D<0 and $|D|_{max}=\min(q_1p_2, p_1q_2)$ if D>0) and is independent of allele frequencies. The correlation coefficient is $r^2=D^2/p_1p_2q_1q_2$. The study reports D', $r^2$, $\chi^2$, and P-values corresponding to $\chi^2$.

Statistical Analysis of Association Study

Genotype frequencies of each SNP and allele frequencies between R and NR will be compared by using the $\chi^2$ test or Fisher exact test. R as a reference group, the odd ratio is performed to test which allele or genotype is risking factor. According to odd ratio, alleles and genotypes associated with responsiveness or non-responsiveness are defined. To evaluate the combined genotypes of multiple SNPs in the same genes or pathway, the $\chi^2$ test or Fisher exact test is also performed. All statistical tests are 2-tailed, and P-values less than 0.05 are considered statistically significant. The analyses are performed using the SAS statistical package version 8.

Results (1) Selected SNPs of CD81 Gene SEQ ID NO: 46

Over the selected 70 Kb chromosomal region, including CD81 gene SEQ ID NO: 46 and extending 30 Kb each to the 5' and 3' flanking regions, eighteen SNPs and one insertion are identified among HCV infected patients of Chinese population. The positions, sequences, and allele frequencies are summarized in Table 2 of FIG. 8. Among theses polymorphic sites, 16 SNPs have minor allele frequency greater than 10% and considered to be informative markers for the association analysis of genetic polymorphism with treatment response.

(2) Association of SNP Markers of CD81 Gene SEQ ID NO: 46 and its Flanking Regions with Treatment Responsiveness of HCV Patients to Interferon-α and Ribavirin Combined Therapy.

Also shown in Table 3 of FIG. 9, among the 19 SNPs, 7 show allelic association with the treatment response status. In five of these seven SNPs the genotype distribution between responder and non-responder are statistically different. The results of statistic analysis are summarized in Tables 4 to 14 in the below.

(3) Association of CD81-SNPrs800136 Allele with Treatment Responsiveness of HCV Patients to Interferon-□ and Ribavirin Combined Therapy Distribution of CD81-SNPrs800136 allele SEQ ID NO: 46 and the status of treatment response are summarized in Table 4 of FIG. 10. The CD81-SNPrs800136T allele SEQ ID NO: 46 is found to be associated with responding status and thus a favorable allele for drug treatment.

(4) Association of CD81-SNPrs800137 Allele SEQ ID NO: 46 with Treatment Responsiveness of HCV Patients to Interferon-α and Ribavirin Combined Therapy.

Distribution of CD81-SNPrs800137 alleles SEQ ID NO: 46 and the status of treatment response are summarized in Table 5 of FIG. 11. The CD81-SNPrs800137T allele SEQ ID NO: 46 is found to be associated with responding status and thus a favorable allele for drug treatment.

(5) Association of CD81-SNPrs800334 SEQ ID NO: 46 with Treatment Responsiveness of HCV Patients to Interferon-α and Ribavirin Combined Therapy.

Distribution of CD81-SNPrs800334 alleles SEQ ID NO: 46, genotypes, and the status of treatment response are summarized in Tables 6 and 7 of FIG. 12. The CD81-SNPrs800334 G allele SEQ ID NO: 46 and the GG genotype are found to be associated with responding status and thus a favorable allele for drug treatment.

(6) Association of CD81-SNPpos1989603 SEQ ID NO: 46 with Treatment Responsiveness of HCV Patients to Interferon-α and Ribavirin Combined Therapy.

Distribution of CD81-SNPpos1989603 alleles SEQ ID NO: 46, genotypes, and the status of treatment response are summarized in Tables 8 and 9 of FIG. 13. The CD81-SNPpos1989603 A allele SEQ ID NO: 46 and the AA genotype are found to be associated with responding status and thus a favorable allele for drug treatment.

(7) Association of CD81-SNPrs2522012 SEQ ID NO: 46 with Treatment Responsiveness of HCV Patients to Interferon-α and Ribavirin Combined Therapy.

Distribution of CD81-SNPrs2522012 alleles SEQ ID NO: 46, genotypes, and the status of treatment response are summarized in Tables 10 and 11 of FIG. 14. The CD81-SNPrs2522012 T allele SEQ ID NO: 46 and the TT genotype are found to be associated with responding status and thus a favorable allele for drug treatment.

(8) Association of CD81-SNPrs2522013 SEQ ID NO: 46 with Treatment Responsiveness of HCV Patients to Interferon-α and Ribavirin Combined Therapy.

Distribution of CD81-SNPrs2522013 alleles SEQ ID NO: 46, genotypes, and the status of treatment response are summarized in Tables 12 and 13 of FIG. 15. The CD81-SNPrs2522013 A allele SEQ ID NO: 46 and the AA genotype are found to be associated with responding status and thus a favorable allele for drug treatment.

(9) Association of CD81-SNPrs800335 SEQ ID NO: 46 with Treatment Responsiveness of HCV Patients to Interferon-α and Ribavirin Combined Therapy.

Distribution of CD81-SNPrs800335 alleles SEQ ID NO: 46, genotypes, and the status of treatment response are summarized in Tables 14 and 15 of FIG. 16. The CD81-SNPrs800335 T allele SEQ ID NO: 46 and the TT genotype are found to be associated with responding status and thus a favorable allele for drug treatment.

(10) Linkage Disequilibrium (LD) Structure of CD81 Gene SEQ ID NO: 46.

Figure 17:
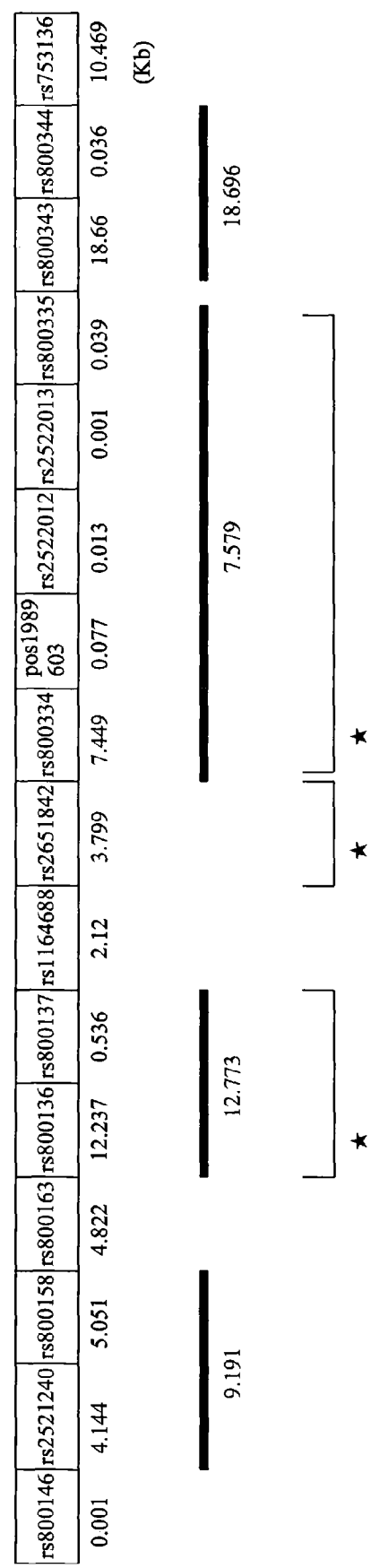
FIG. 17 shows the haplotype blocks that encompass the 5', 3', and the intragenic region of CD 81 gene SEQ ID NO: 46, and SNPs showing to be associated with response to interferon-α and ribavirin combined therapy.

The LD structure of CD81 gene SEQ ID NO: 46 and its flanking regions extended 30 Kb each to the 5' and 3' ends are constructed by genotypes of the selected 16 informative SNPs. In this 70 Kb chromosomal fragment of DNA, 9 haplotype blocks are identified as depicted in FIG. 17.

(11) Association of Haplotypes in Haplotype Block 4 with Treatment Responsiveness of HCV Patients to Interferon-α and Ribavirin Combined Therapy Two SNPs are located in haplotype block 4, and the distribution of the haplotype and the status of treatment response are summarized in Table 16 of FIG. 18. The GG haplotype is found to be associated with responding status and thus a favorable haplotype for drug treatment.

(12) Association of Haplotypes in Haplotype Block 7 with Treatment Responsiveness of HCV Patients to Interferon-□ and Ribavirin Combined Therapy Haplotypes of the seventh haplotype block are constructed by the five informative SNP markers. Distribution of the haplotype and the status of treatment response are summarized in Table 17 of FIG. 19. The TGGCC haplotype is found to be associated with responding status and thus a favorable haplotype for drug treatment. In contrast, the GATAT haplotype is found to be associated with non-responsiveness and a non-favorable factor for drug treatment.

While the present invention has been described in conjunction with preferred embodiments thereof, it is evident that many alternatives, modifications and variations will be apparent to those skilled in the art. Accordingly, it is intended to embrace all such alternatives, modifications and variations that fall within the spirit and scope thereof as set forth in the appended claims.

What is claimed is:

1. A method for detecting a propensity of an HCV-infected individual to respond effectively to treatment of interferon-α and ribavirin combined therapy, the method comprising: detecting the presence of a single nucleotide polymorphism in a CD81 gene (SEQ ID NO: 46) and determining that said individual has said propensity to respond effectively to said, treatment of interferon-α and ribavirin combined therapy if said single nucleotide polymorphism is present, wherein said single nucleotide polymorphism is selected from the group consisting of a T at rs800136, a T at rs800137, a G at rs800334, an A at pos1989603, a T at rs2522012, an A at rs2522013, and a T at rs800335.

2. The method of claim 1, wherein the step of detecting the presence of said single nucleotide polymorphism further comprises the step of analyzing a polynucleotide sample to determine the presence of said single nucleotide polymorphism by performing a process selected from the group consisting of detection of specific hybridization, measurement of allele size, restriction fragment length polymorphism analysis, allele-specific hybridization analysis, single base primer extension reaction, and sequencing of an amplified polynucleotide.

3. A method for detecting a propensity of an HCV-infected individual to respond effectively to treatment of interferon-α and ribavirin combined therapy, the method comprising: detecting the presence of a haplotype in a CD81 gene (SEQ ID NO: 46) and its flanking regions and determining that said individual has said propensity to respond effectively to said treatment of interferon-α and ribavirin combined therapy if said haplotype is present, wherein said haplotype is a CC haplotype for single nucleotide polymorphisms at rs800136 and rs800137 or a TGGCC haplotype for single nucleotide polymorphisms at rs800334, pos1989603, rs2522012, rs2522013 and rs800335.

* * * * *